United States Patent
Yoon et al.

(10) Patent No.: US 11,001,615 B2
(45) Date of Patent: May 11, 2021

(54) MUTATED TAU PROTEIN FRAGMENT AND USE THEREOF

(71) Applicant: ADEL INC., Seoul (KR)

(72) Inventors: Seung-Yong Yoon, Seoul (KR); Na-Young Kim, Seoul (KR); Dong-Hou Kim, Yeongwol-gun (KR)

(73) Assignee: ADEL INC., Seoul (KR)

( * ) Notice: Subject to any disclaimer, the term of this patent is extended or adjusted under 35 U.S.C. 154(b) by 0 days.

(21) Appl. No.: 16/472,022

(22) PCT Filed: Dec. 20, 2017

(86) PCT No.: PCT/KR2017/015137
§ 371 (c)(1),
(2) Date: Jun. 20, 2019

(87) PCT Pub. No.: WO2018/117647
PCT Pub. Date: Jun. 28, 2018

(65) Prior Publication Data
US 2019/0330293 A1 Oct. 31, 2019

(30) Foreign Application Priority Data
Dec. 21, 2016 (KR) .................. 10-2016-0175705

(51) Int. Cl.
| | | |
|---|---|---|
| *C07K 14/47* | (2006.01) | |
| *A61P 25/28* | (2006.01) | |
| *A61K 39/00* | (2006.01) | |
| *C07K 16/18* | (2006.01) | |
| *G01N 33/68* | (2006.01) | |
| *A61K 38/00* | (2006.01) | |

(52) U.S. Cl.
CPC ...... *C07K 14/4711* (2013.01); *A61K 39/0007* (2013.01); *A61P 25/28* (2018.01); *C07K 16/18* (2013.01); *G01N 33/6896* (2013.01); *A61K 38/00* (2013.01); *C07K 2317/76* (2013.01); *G01N 2800/2821* (2013.01); *G01N 2800/2835* (2013.01)

(58) Field of Classification Search
None
See application file for complete search history.

(56) References Cited

U.S. PATENT DOCUMENTS

| | | | | |
|---|---|---|---|---|
| 2004/0110938 A1* | 6/2004 | Parekh | ................... | C07K 14/47 536/23.5 |
| 2007/0098776 A1* | 5/2007 | Fikes | ................... | A61K 9/0019 424/450 |
| 2010/0015724 A1* | 1/2010 | Hornbeck | .............. | C07K 16/44 436/501 |
| 2013/0251731 A1* | 9/2013 | Lee | .......................... | C12Q 1/48 424/158.1 |
| 2014/0302046 A1* | 10/2014 | Sigurdsson | ............. | A61P 25/00 424/139.1 |
| 2018/0282401 A1 | 10/2018 | Novak et al. | | |

FOREIGN PATENT DOCUMENTS

KR   10-2014-0063853 A   5/2014

OTHER PUBLICATIONS

Sofia Lopes, et al., "Tau protein is essential for stress-induced brain pathology", PNAS, 2016, pp. E3755-E3763, vol. 113, No. 26.
Tara E. Tracy, et al., "Acetylated Tau Obstructs KIBRA-Mediated Signaling in Synaptic Plasticity and Promotes Tauopathy-Related Memory Loss", Neuron, Apr. 20, 2016, pp. 245-260, vol. 90.
Todd J. Cohen, et al., "The acetylation of tau inhibits its function and promotes pathological tau aggregation", Nature Communications, Mar. 22, 2011, pp. 1-9, vol. 2, Article No. 252.
David J. Irwin, et al., "Acetylated tau, a novel pathological signature in Alzheimer's disease and other tauopathies", Brain, 2012, pp. 807-818, vol. 135.
International Search Report for PCT/KR2017/015137 dated Mar. 29, 2018 [PCT/ISA/210].

* cited by examiner

*Primary Examiner* — Adam Weidner
(74) *Attorney, Agent, or Firm* — Sughrue Mion, PLLC

(57) ABSTRACT

The present invention relates to a mutated tau protein fragment and a use thereof. The mutated tau protein fragment of the present invention consists of 12 amino acids and thus can easily be prepared. In addition, when the mutated tau protein fragment is injected into an individual as an antigen, a neutralizing antibody against the mutated tau protein is generated. Moreover, the mutated tau protein fragment reduces the aggregation of abnormal tau proteins. Accordingly, the mutated tau protein fragment of the present invention can be effectively used for the prevention or treatment of degenerative neurological diseases.

2 Claims, 26 Drawing Sheets

Specification includes a Sequence Listing.

[Fig. 1]
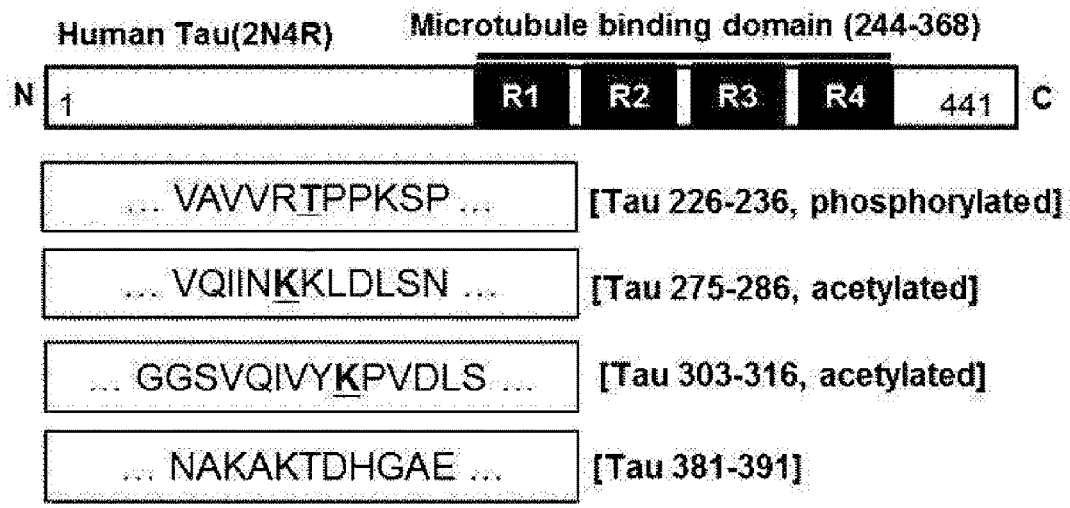
[Fig. 2]
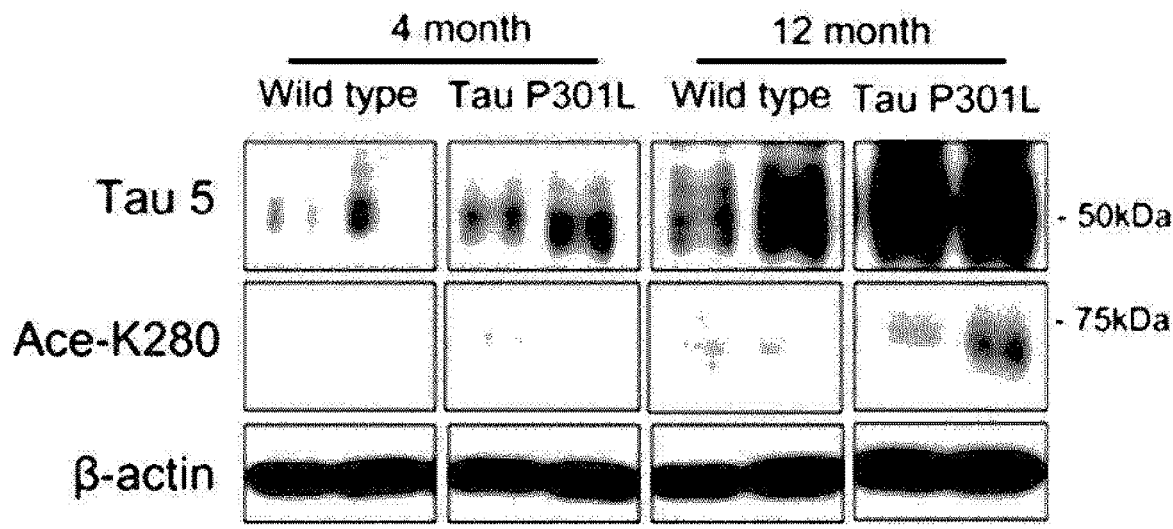

[Fig. 3]
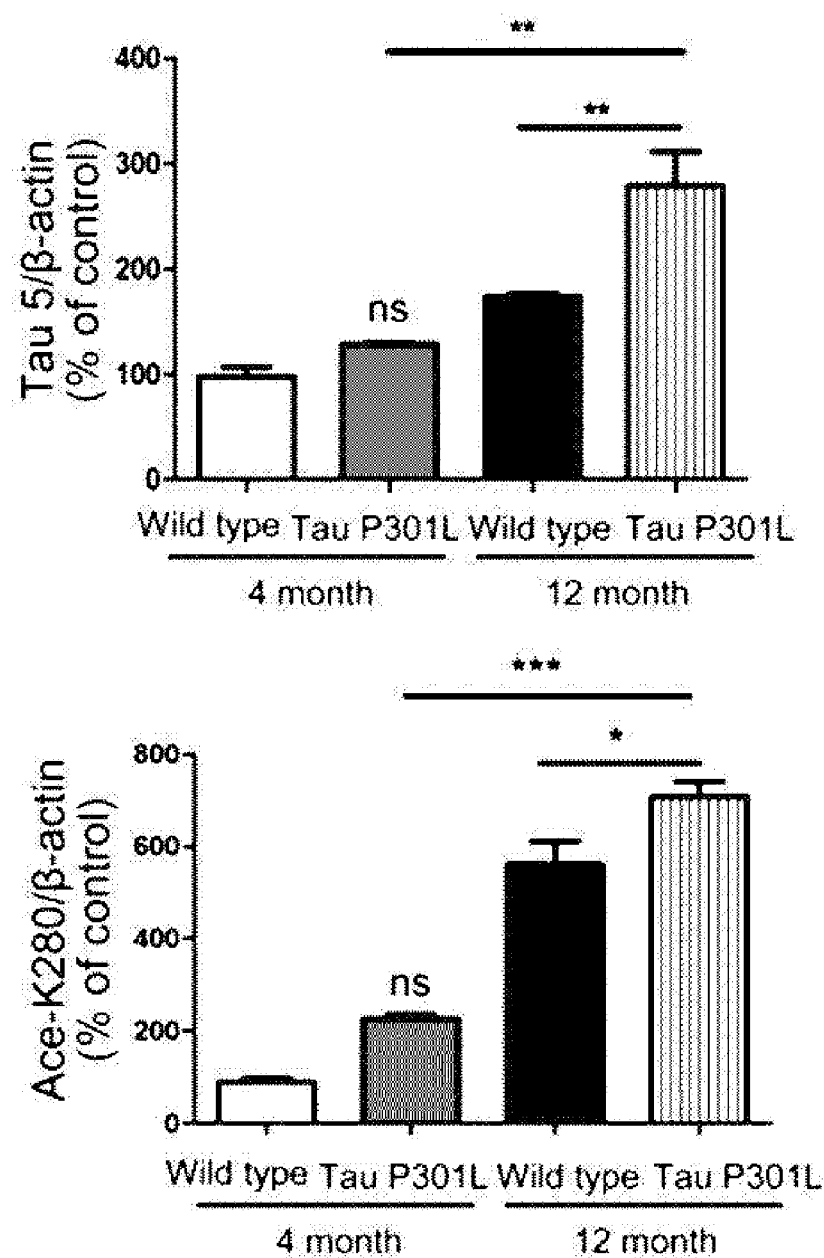

[Fig. 4]
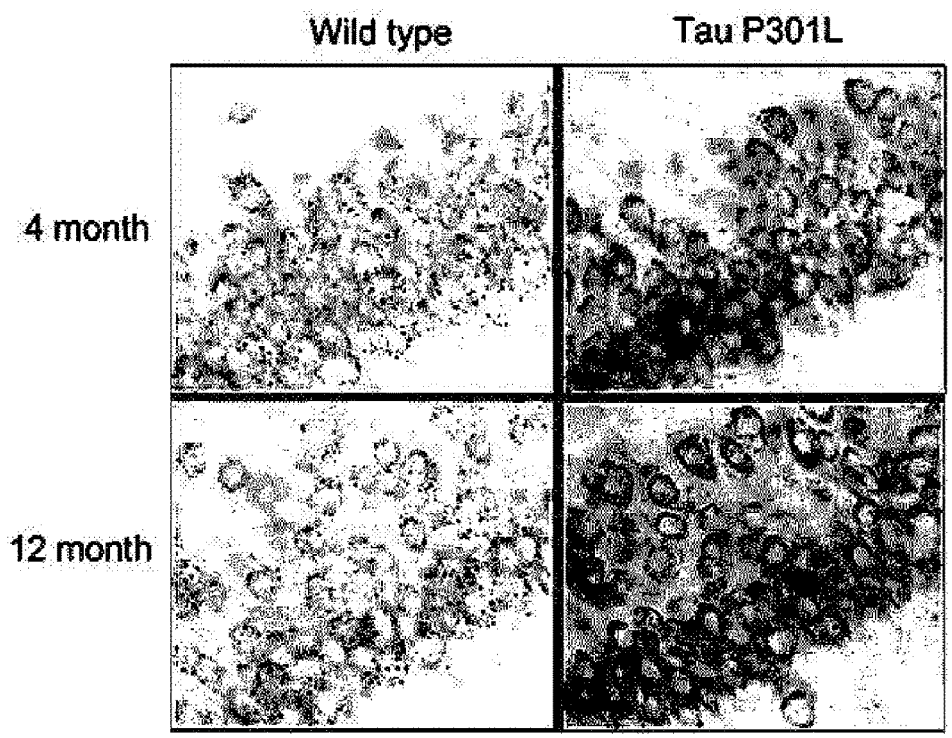
[Fig. 5]
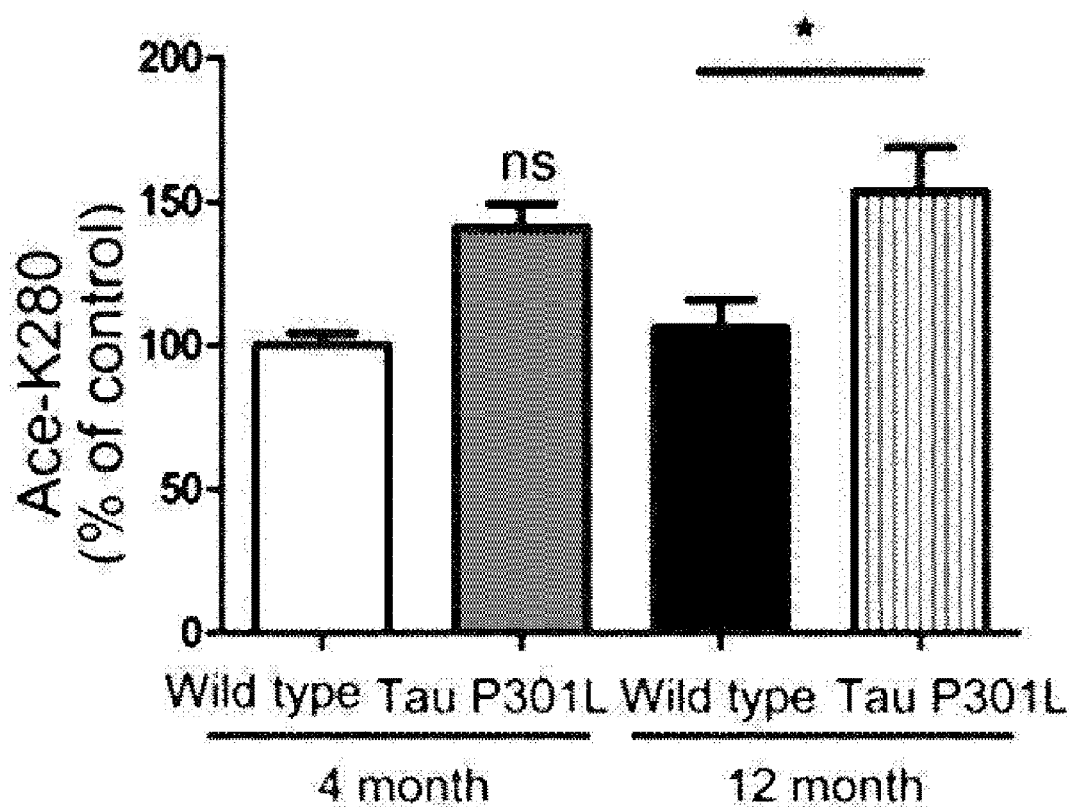

[FIG. 6a]
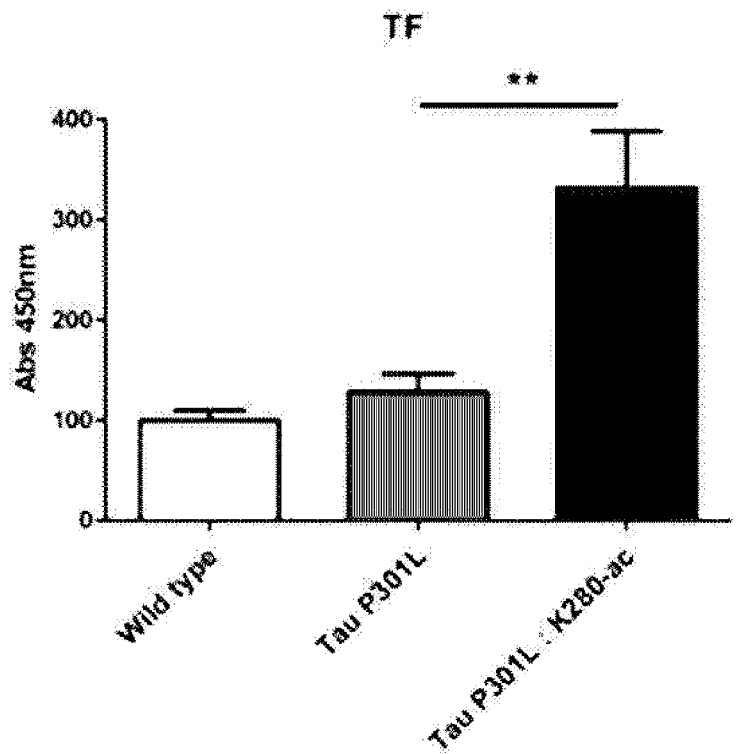
[Fig. 6b]
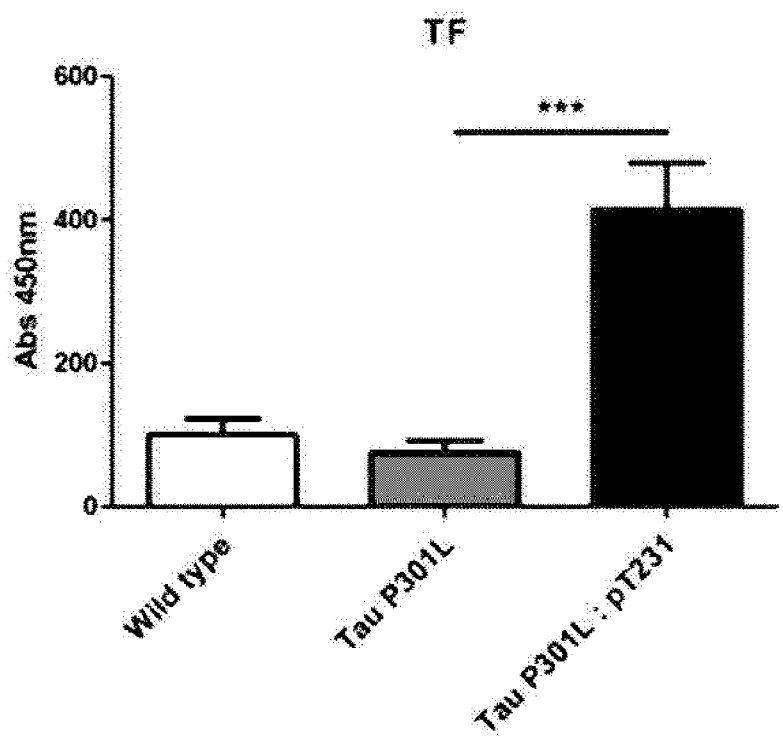

[Fig. 6c]
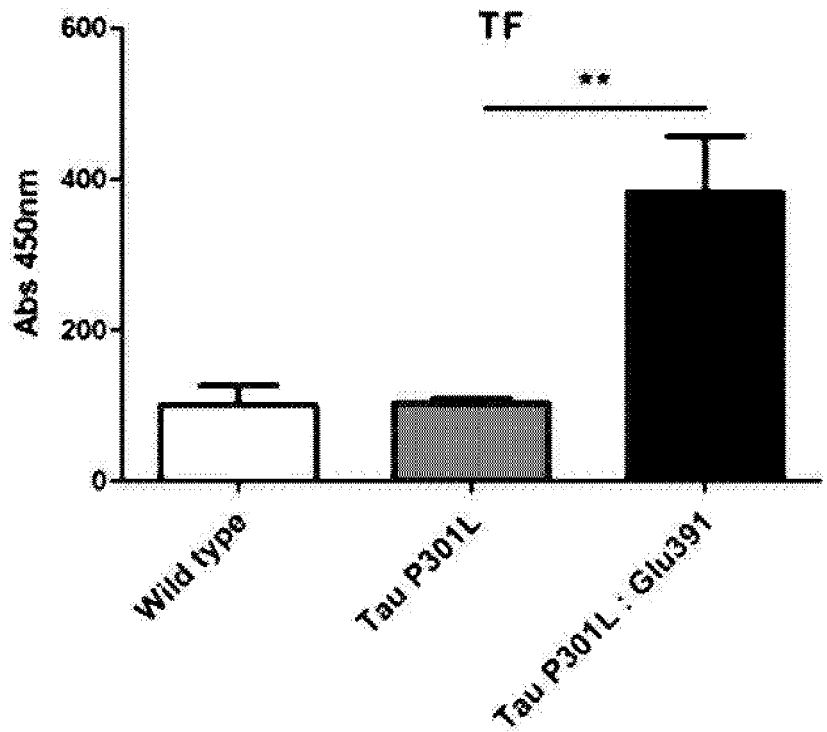
[Fig. 6b]
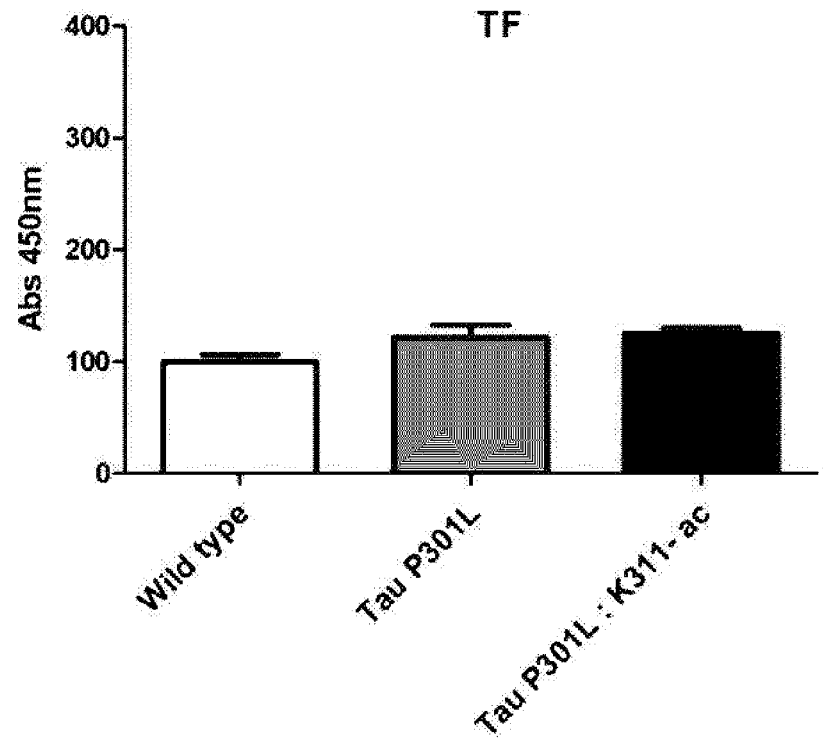

[Fig. 6e]
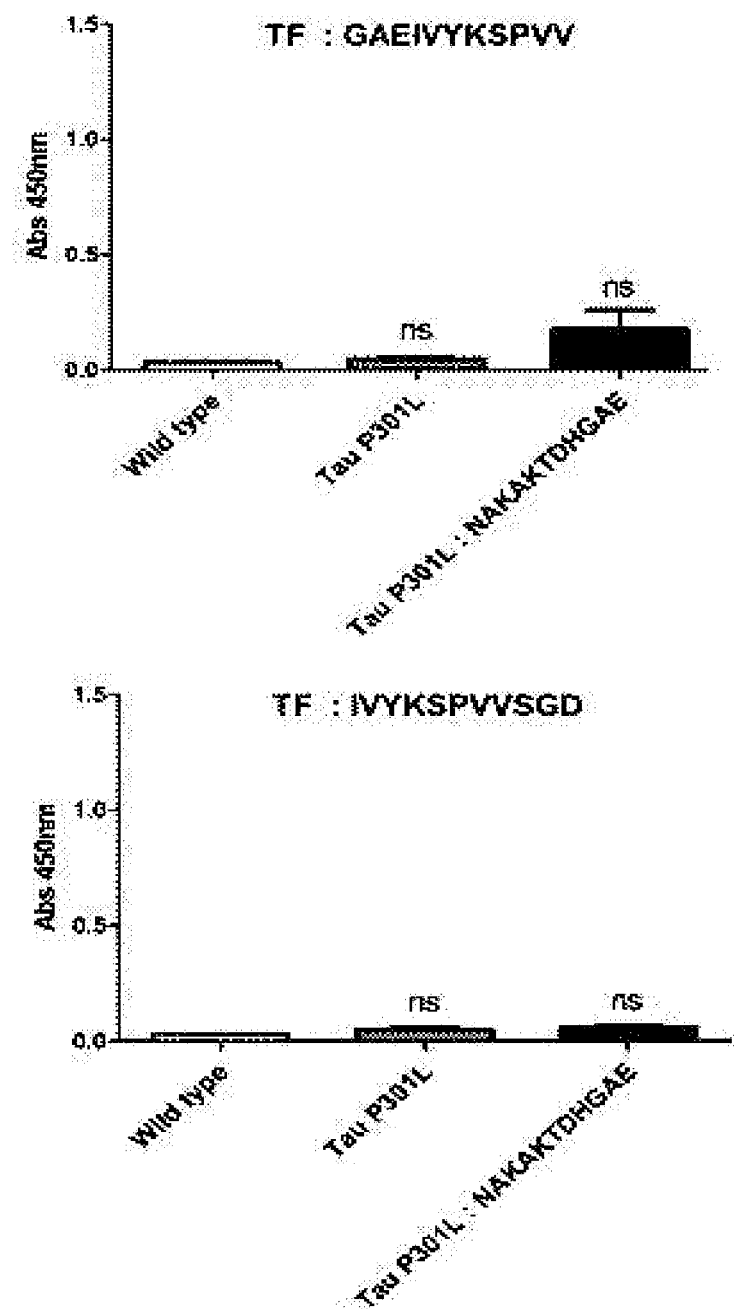

[Fig. 7]
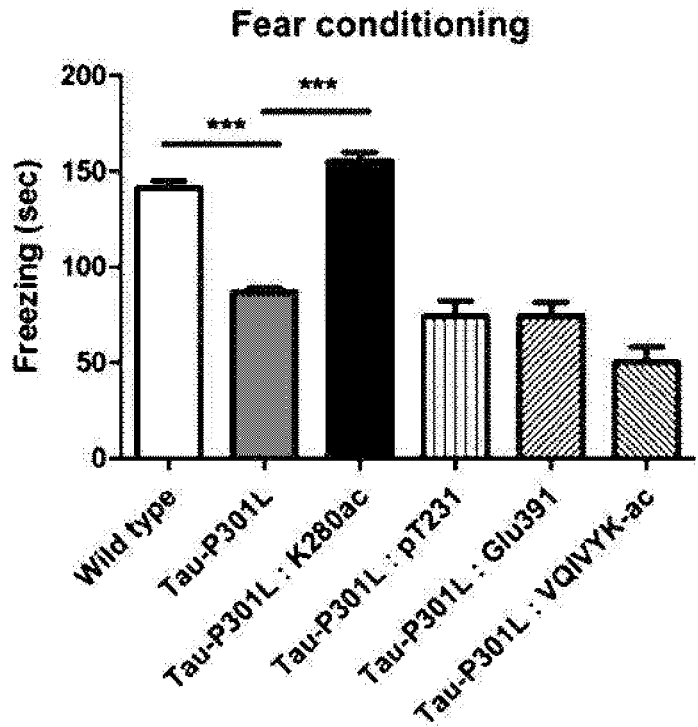
[Fig. 8]
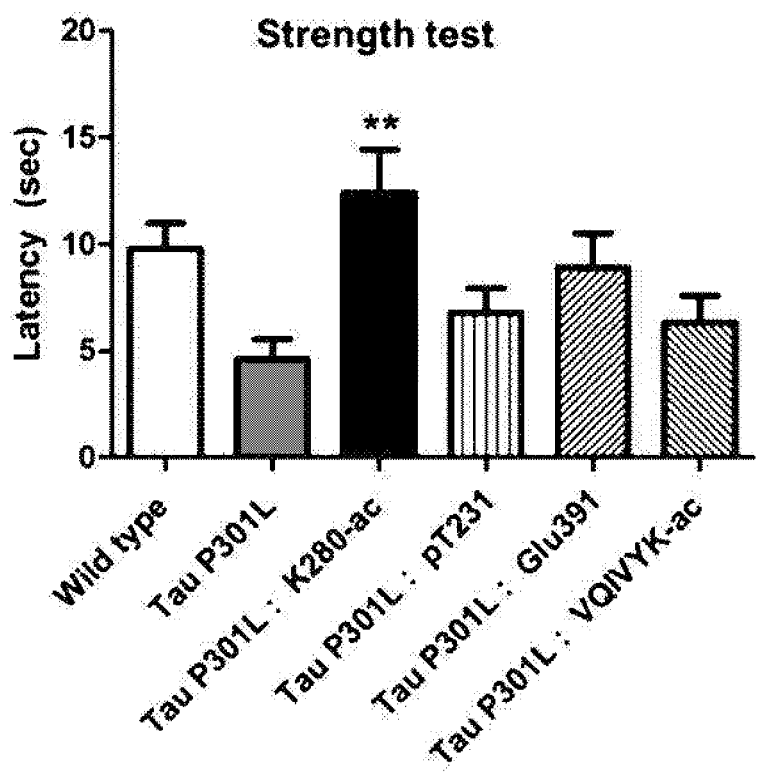

[Fig. 9]
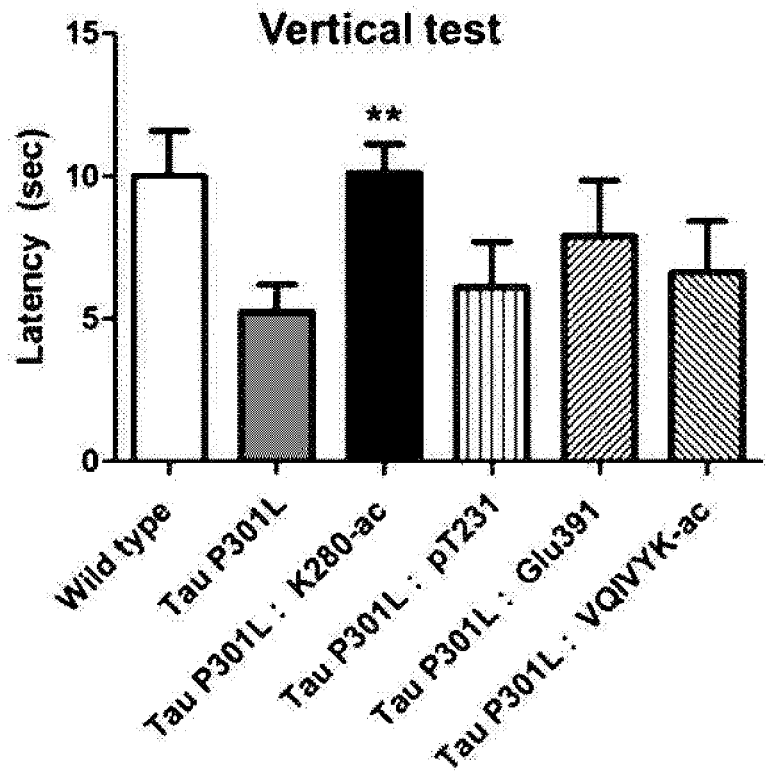
[Fig. 10]
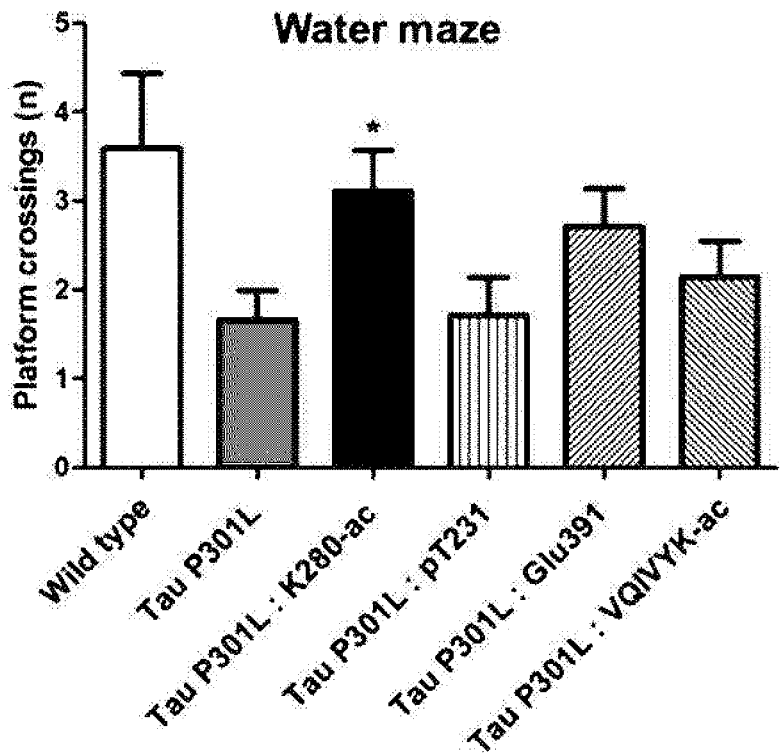

[Fig. 11]
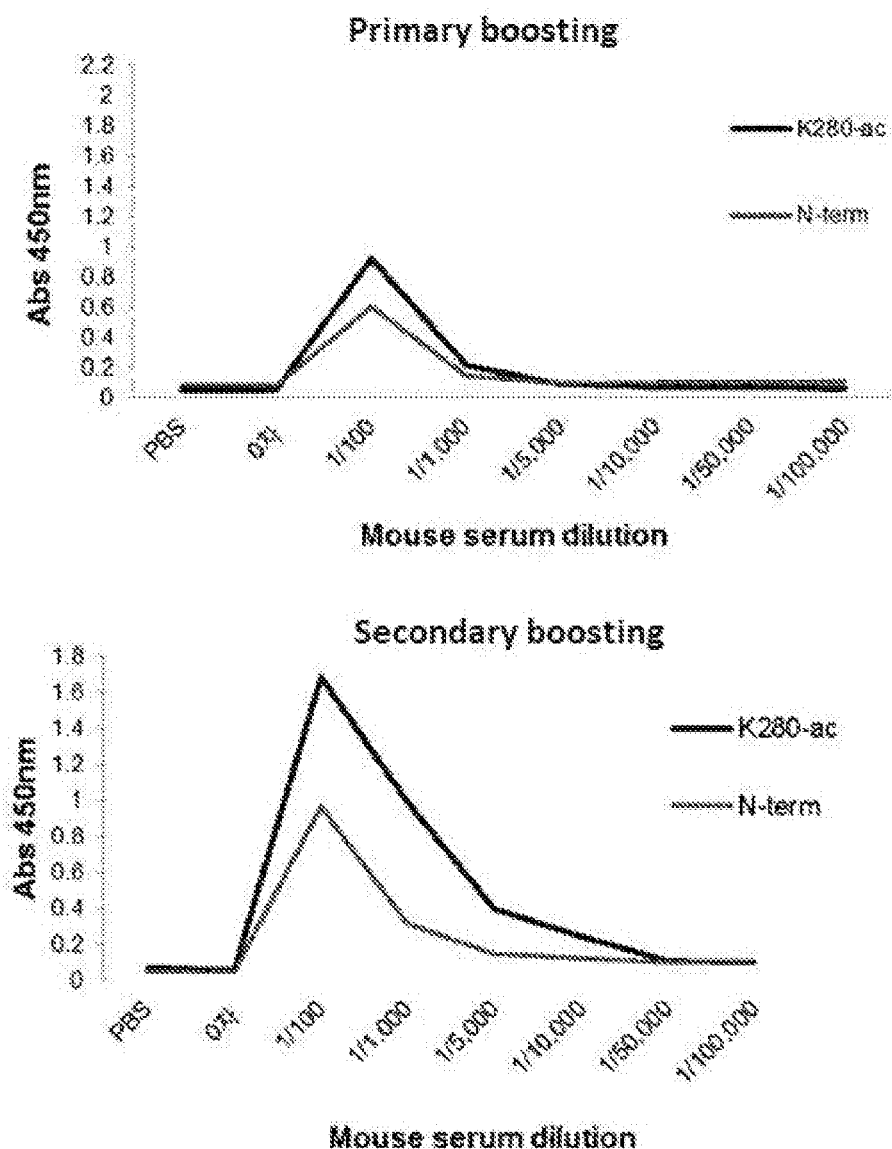

[Fig. 12]
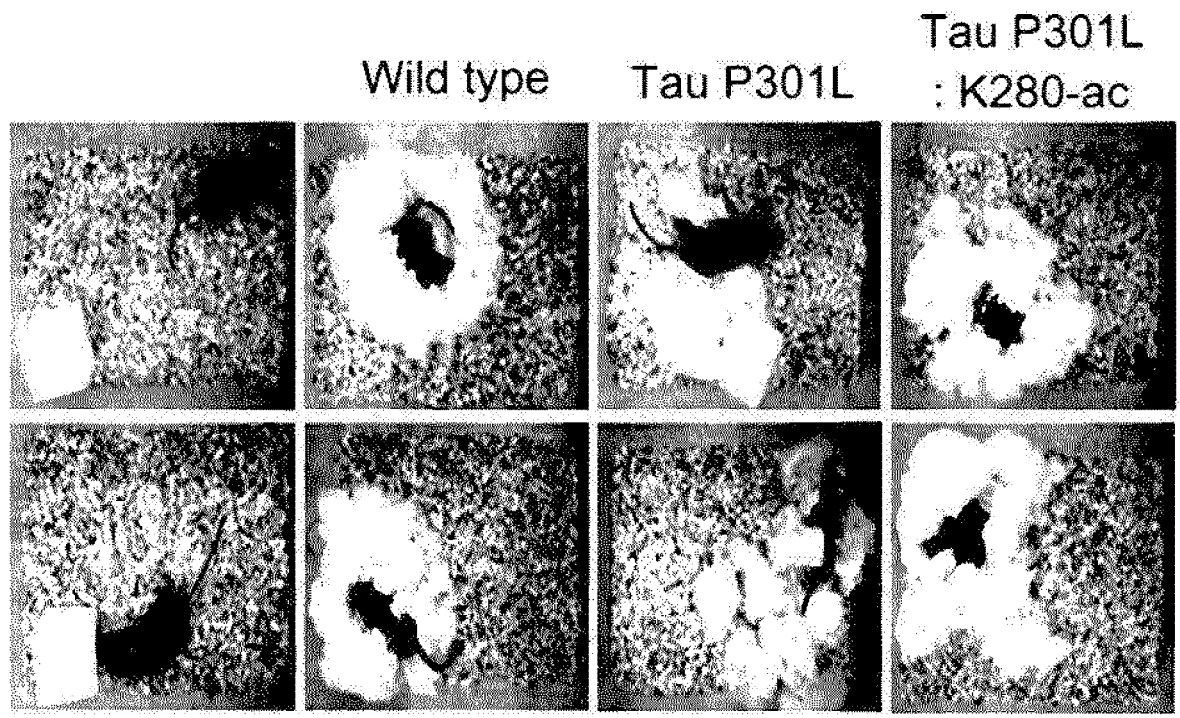
[Fig. 13]
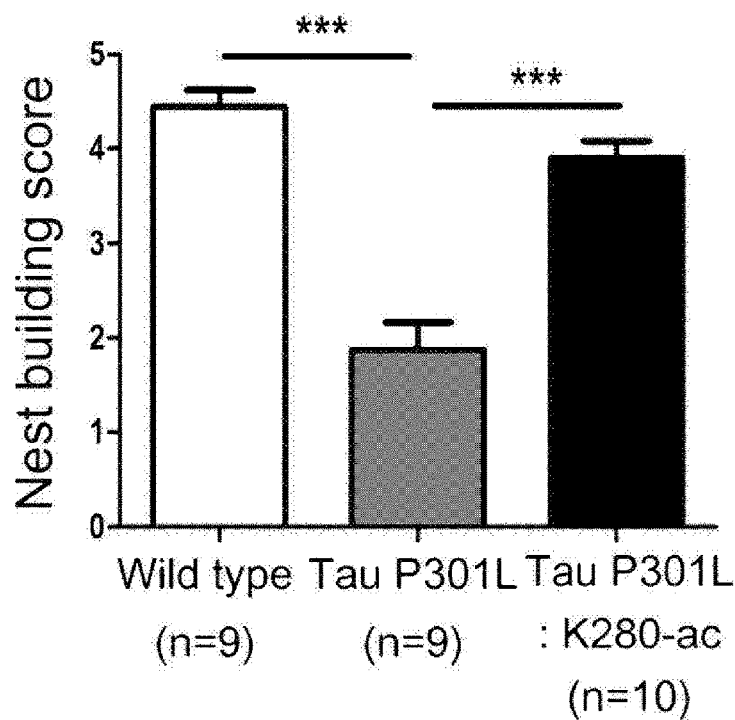

[Fig. 14]
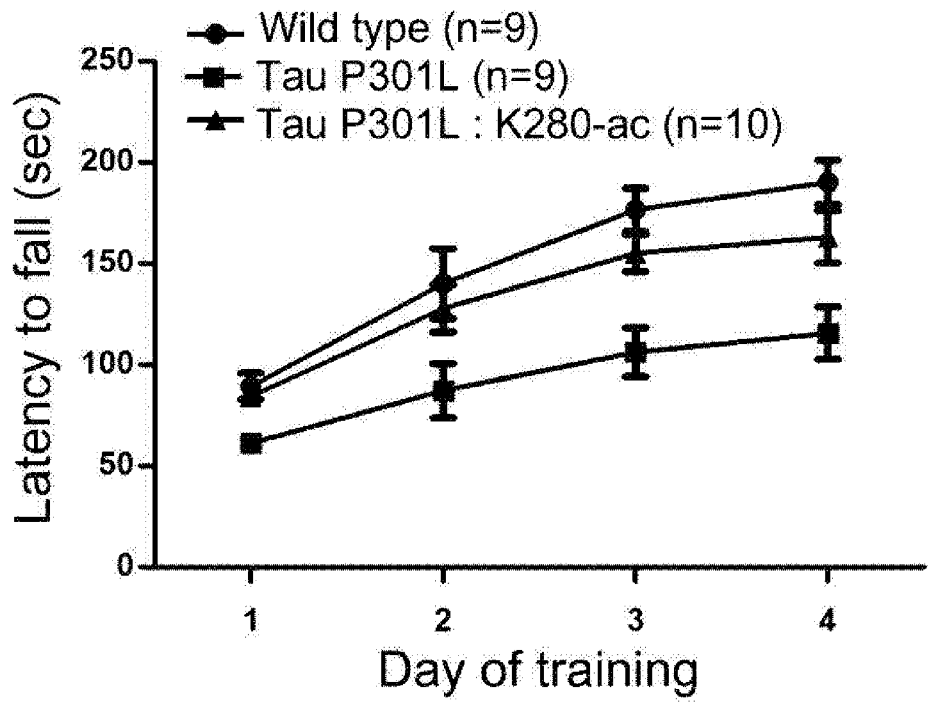
[Fig. 15]
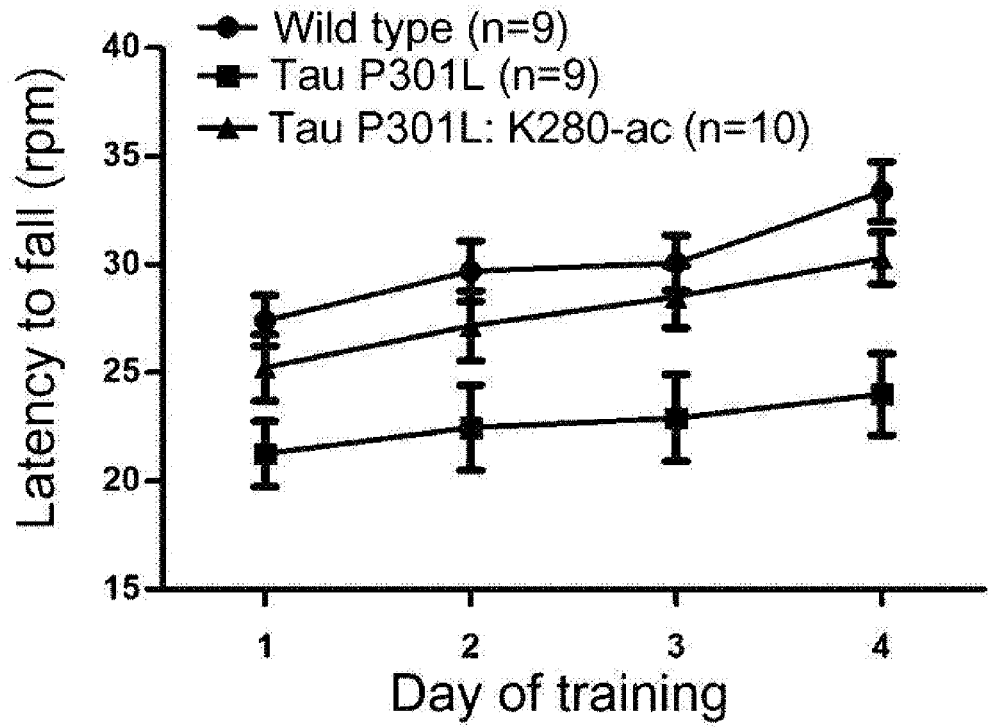

[Fig. 16]
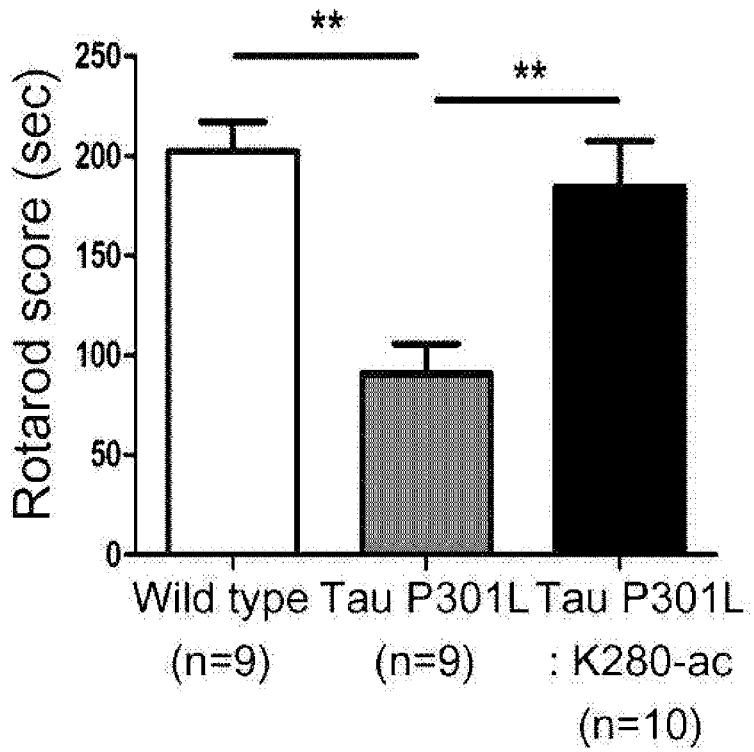
[Fig. 17]
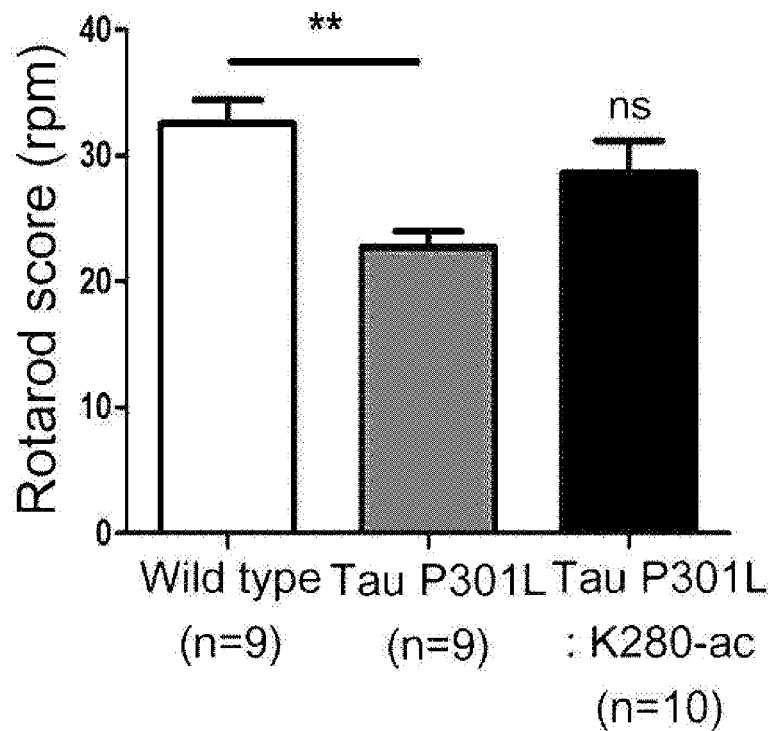

[Fig. 18]
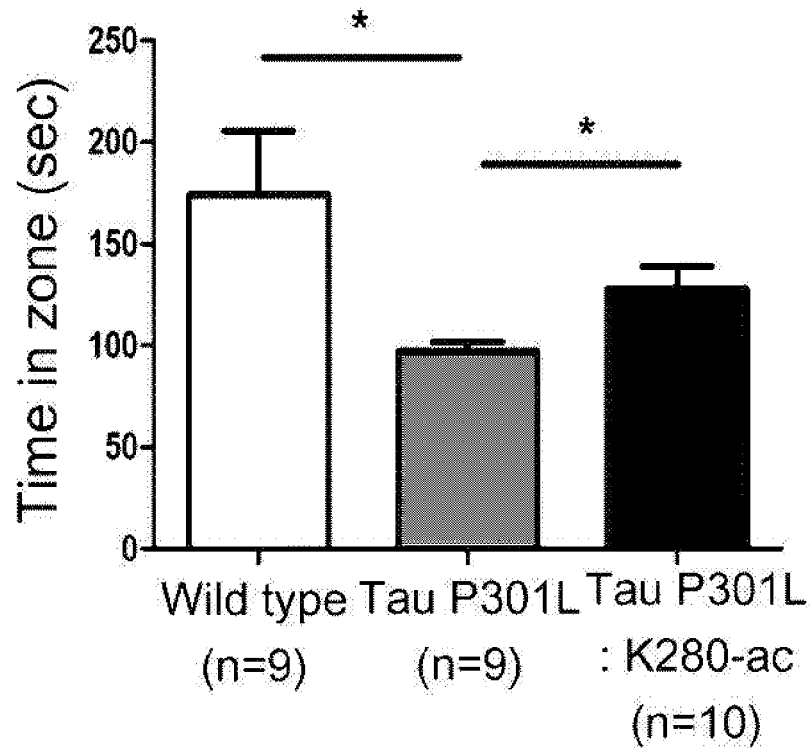
[Fig. 19]
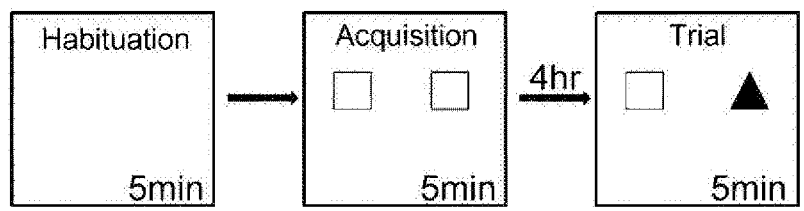
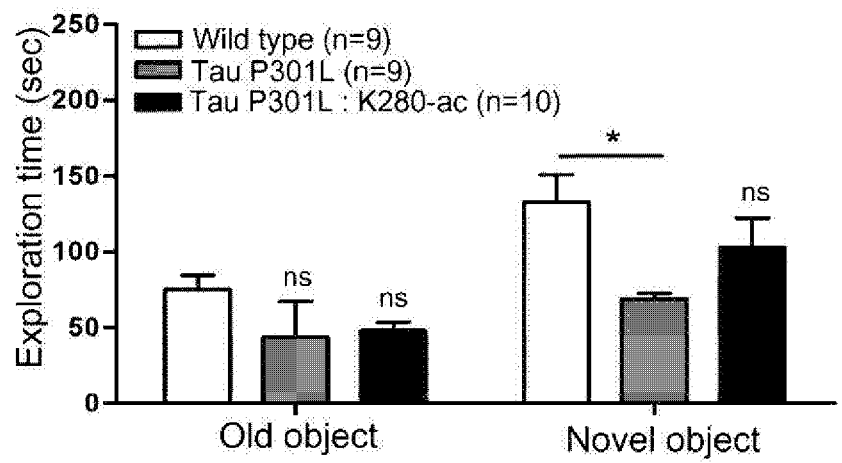

[Fig. 20]
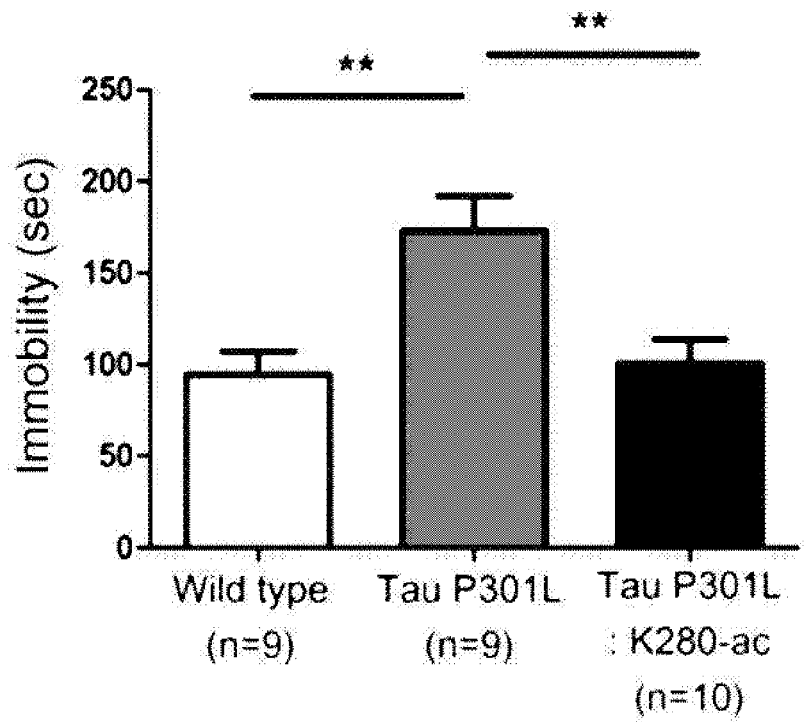
[Fig. 21]
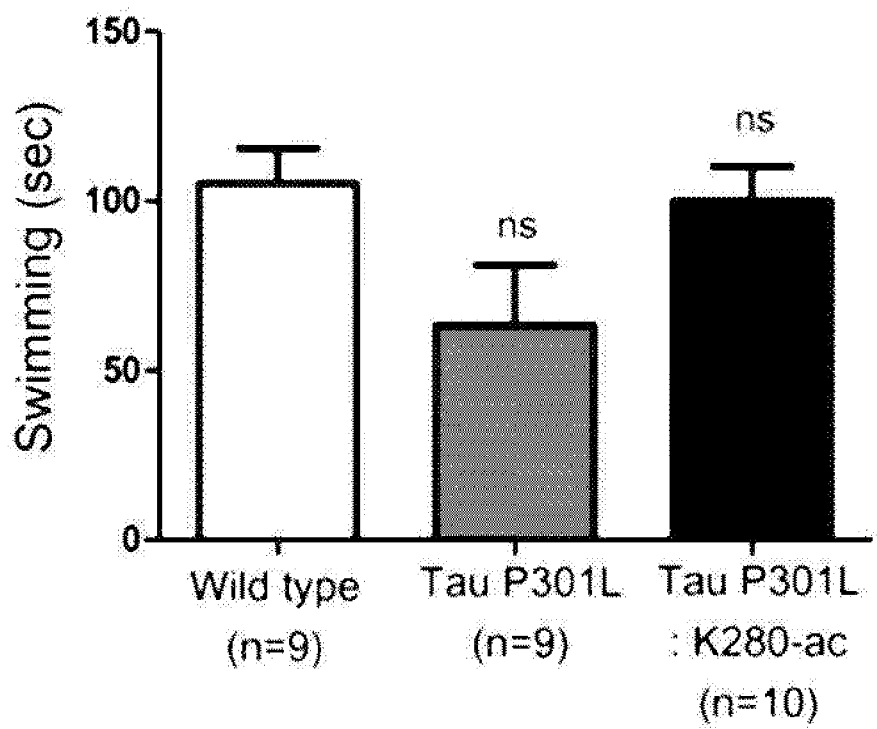

[Fig. 22]
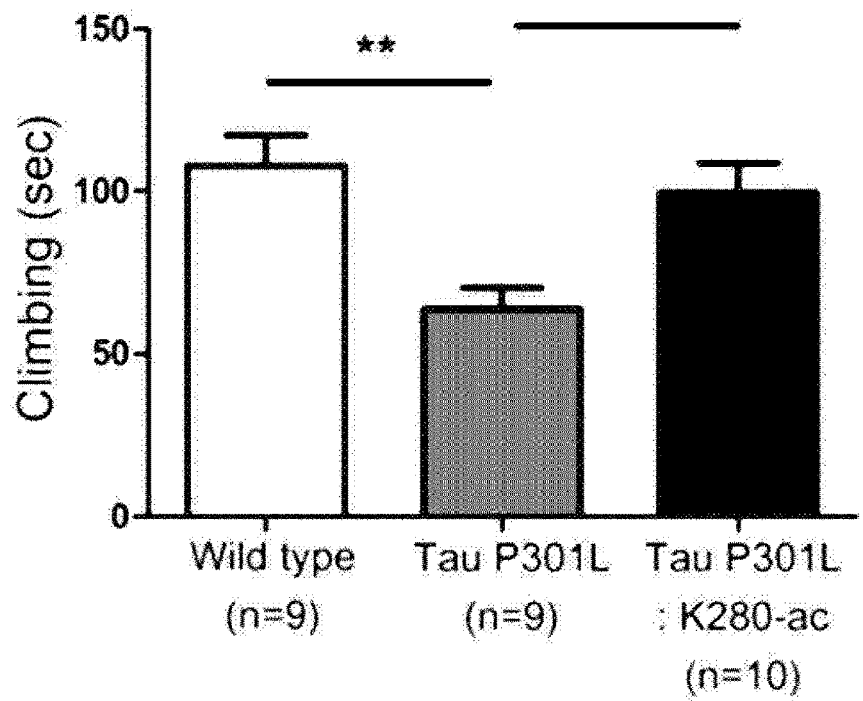
[Fig. 23]
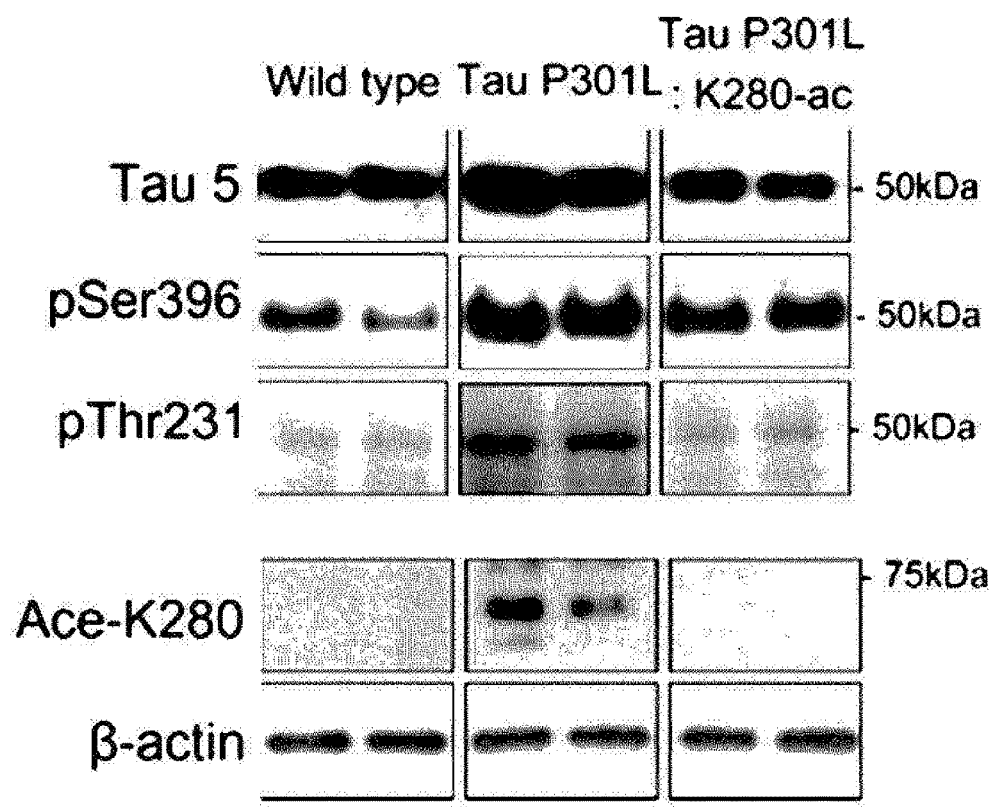

[Fig. 24]
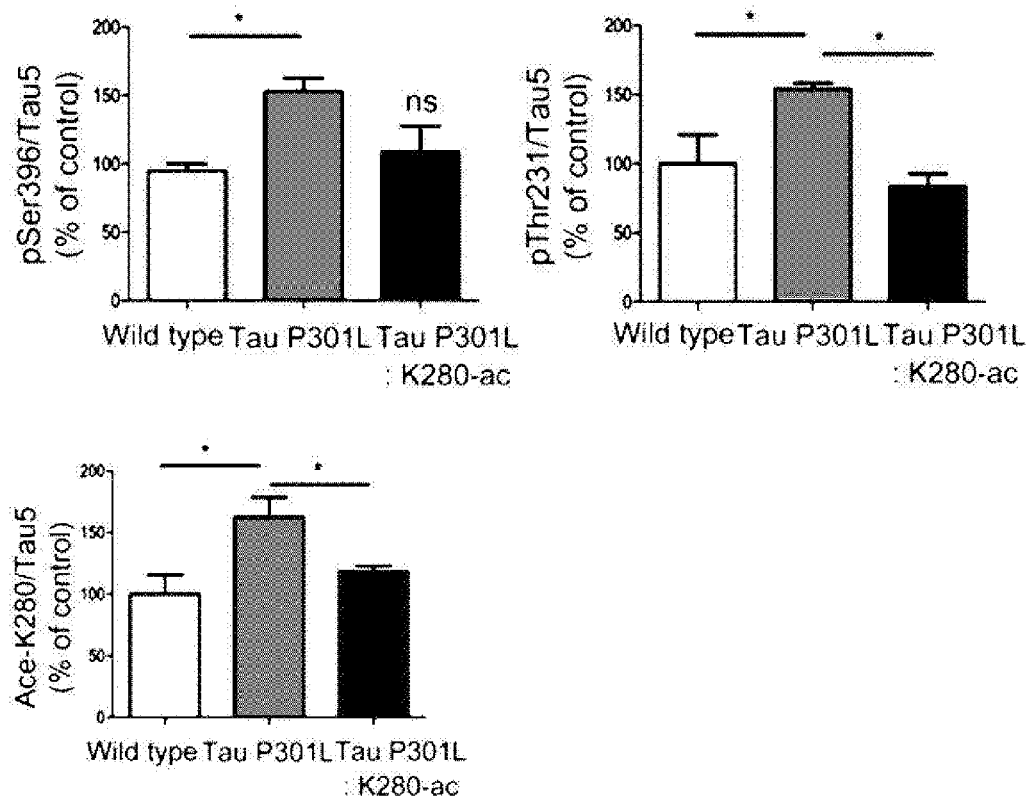

[Fig. 25]
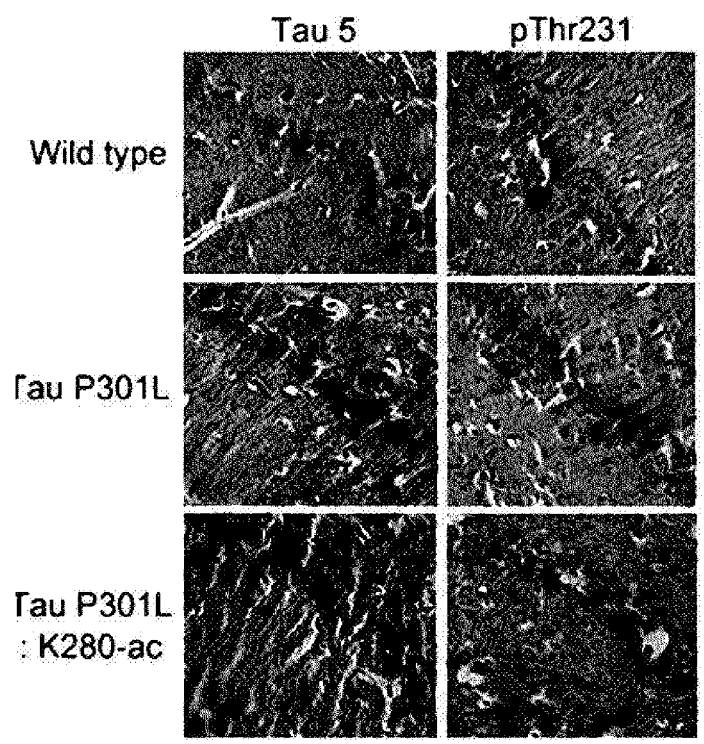

[Fig. 26]
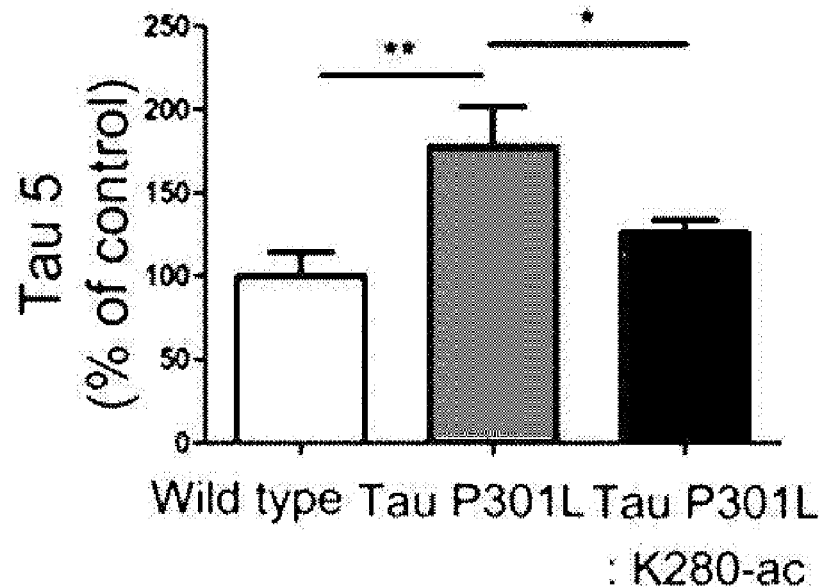
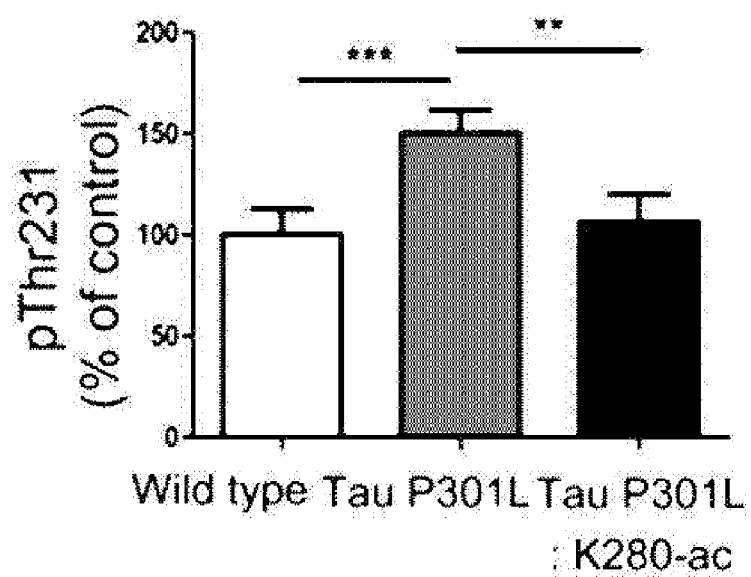

[Fig. 27]
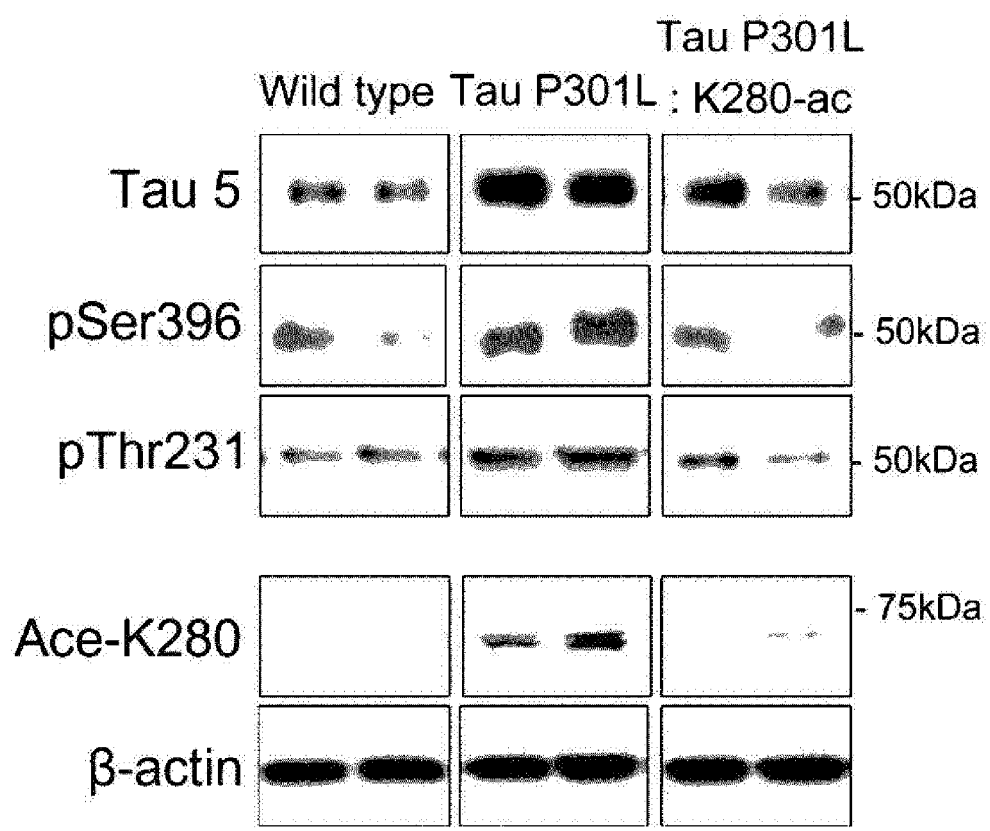

[Fig. 28]
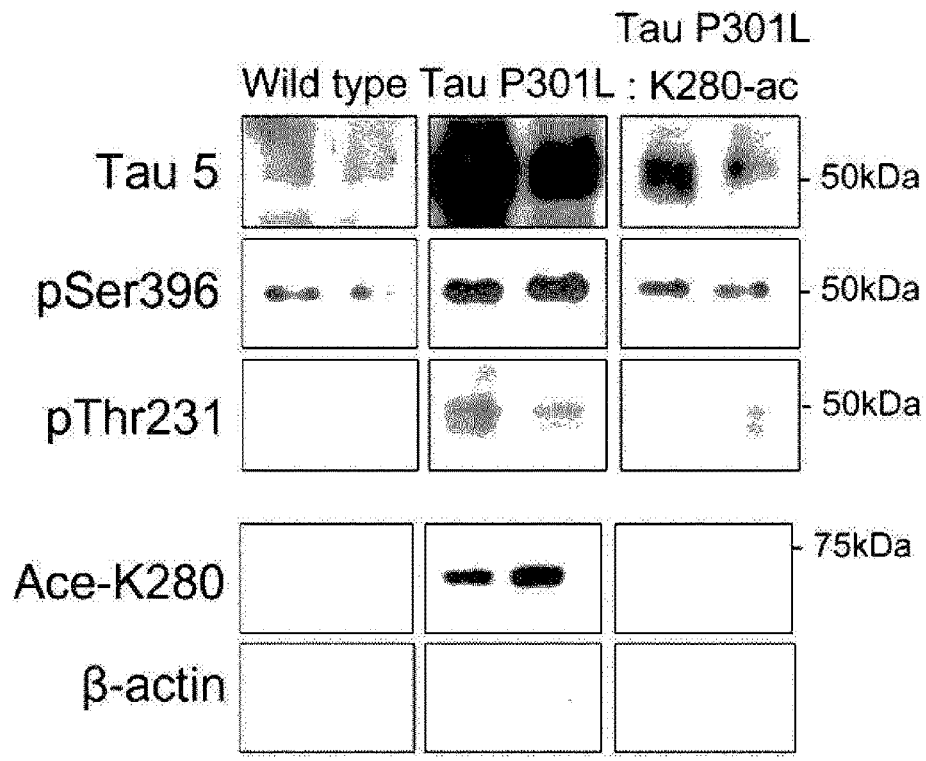
[Fig. 29]
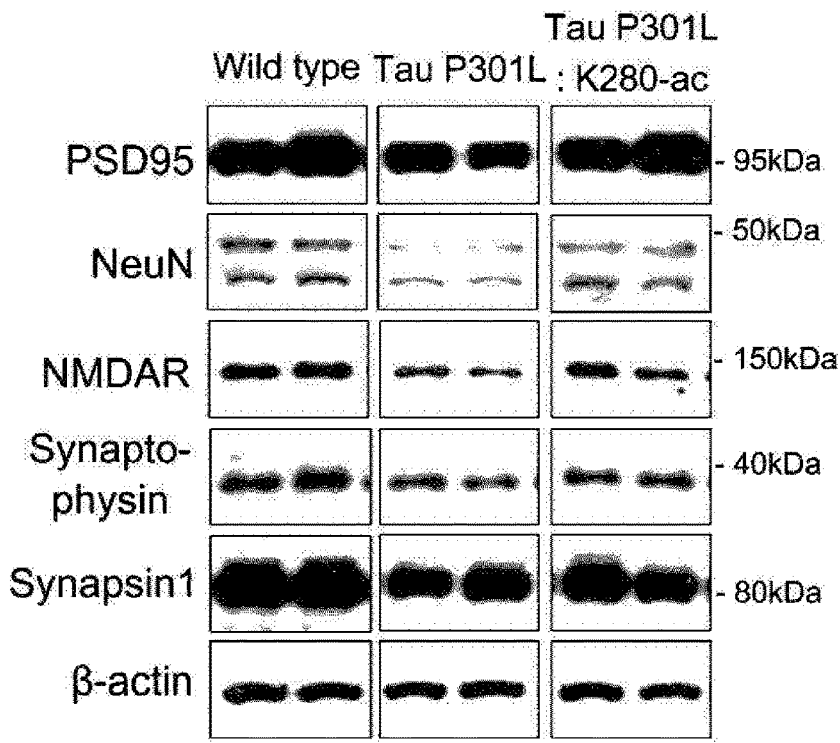

[Fig. 30]
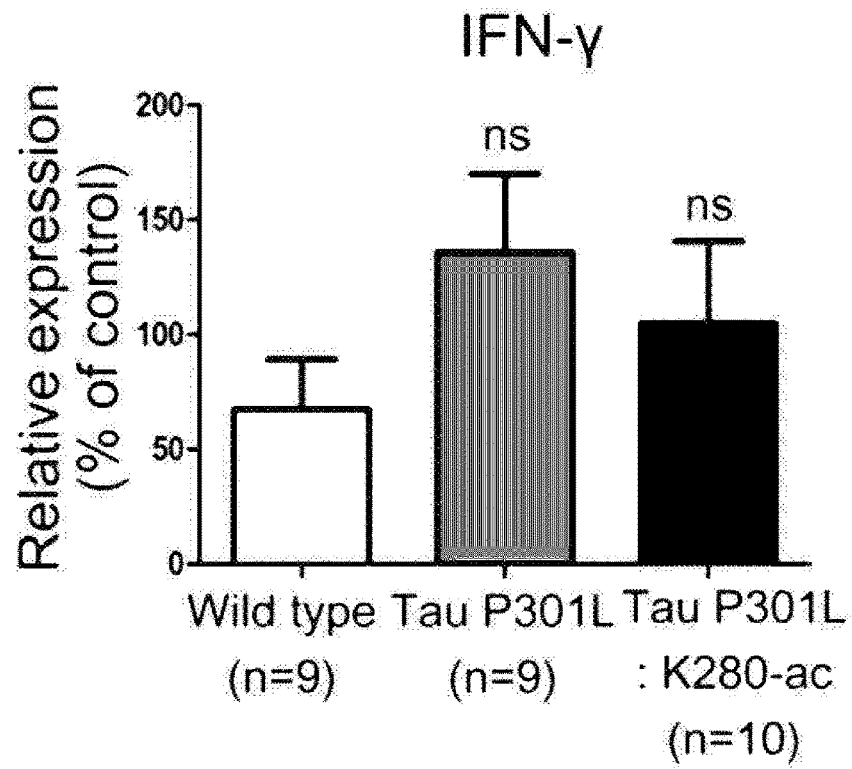
[Fig. 31]
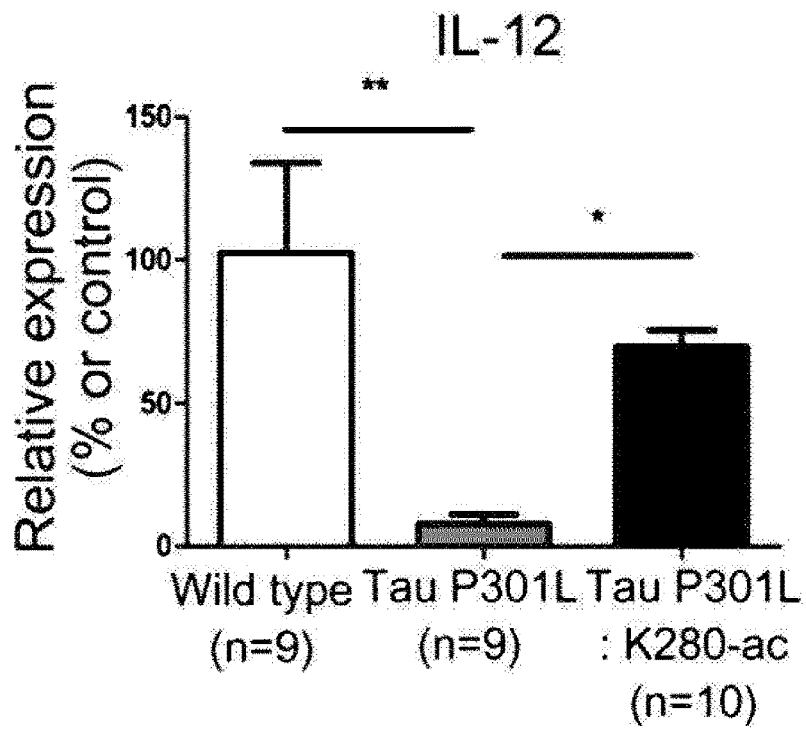

[Fig. 32]
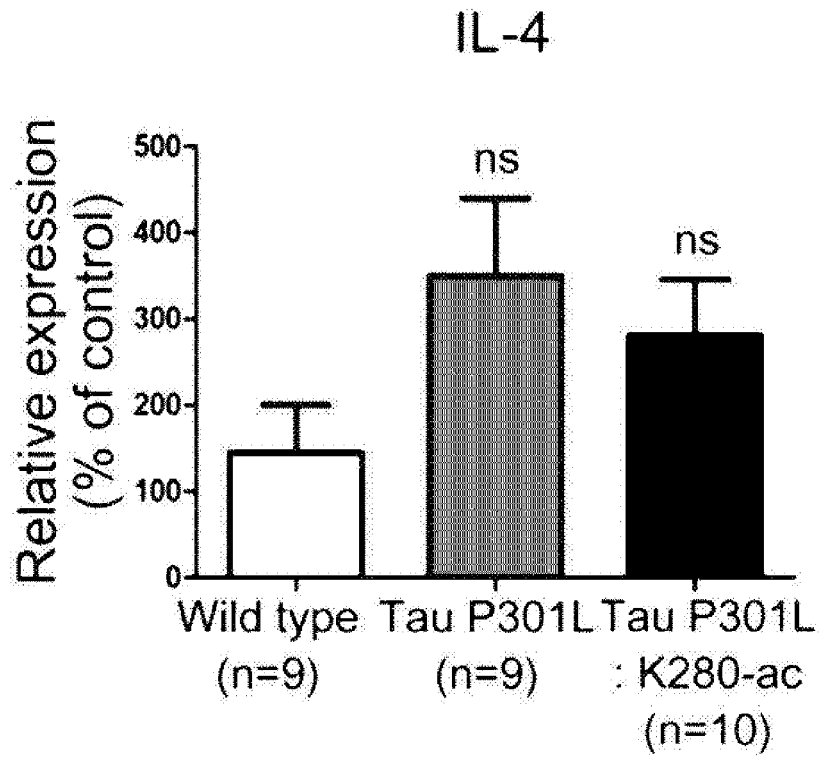
[Fig. 33]
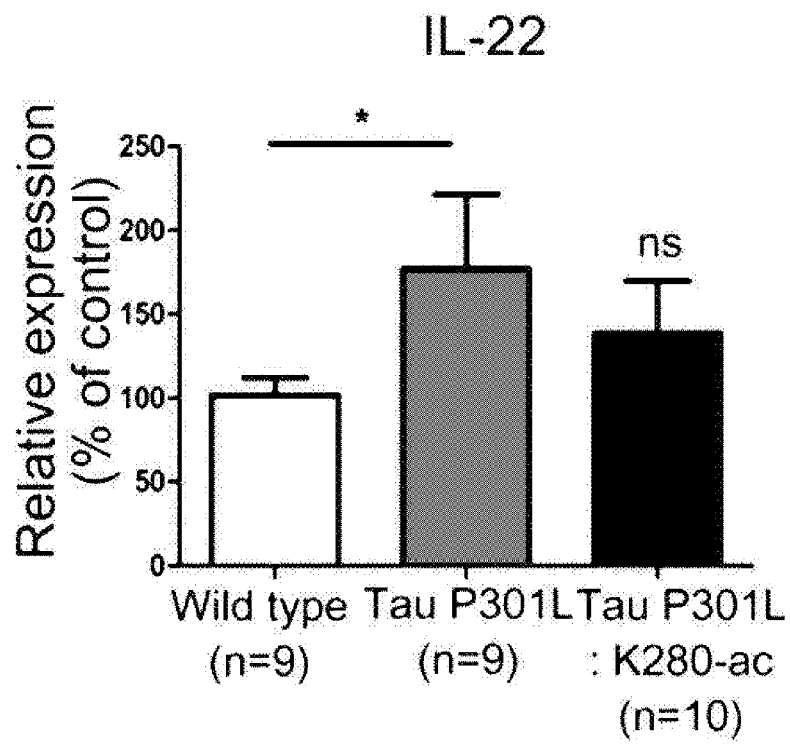

[Fig. 34]
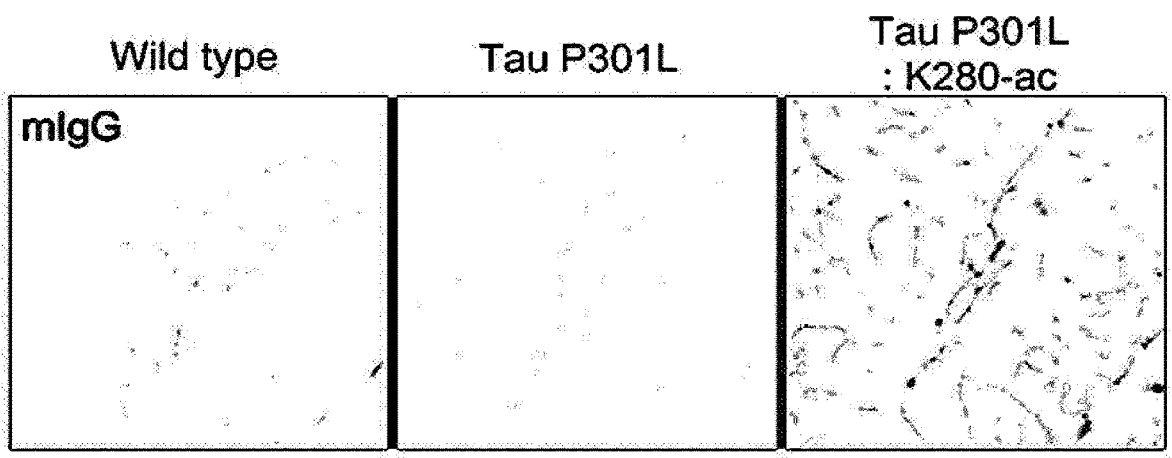
[Fig. 35]
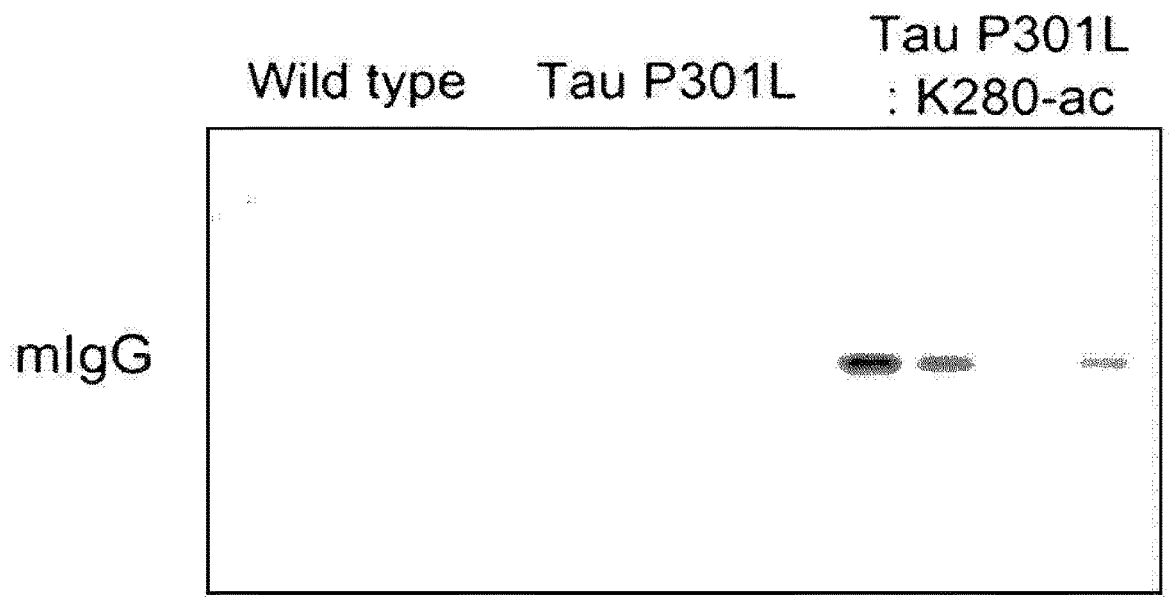

[Fig. 36]
[도 37]
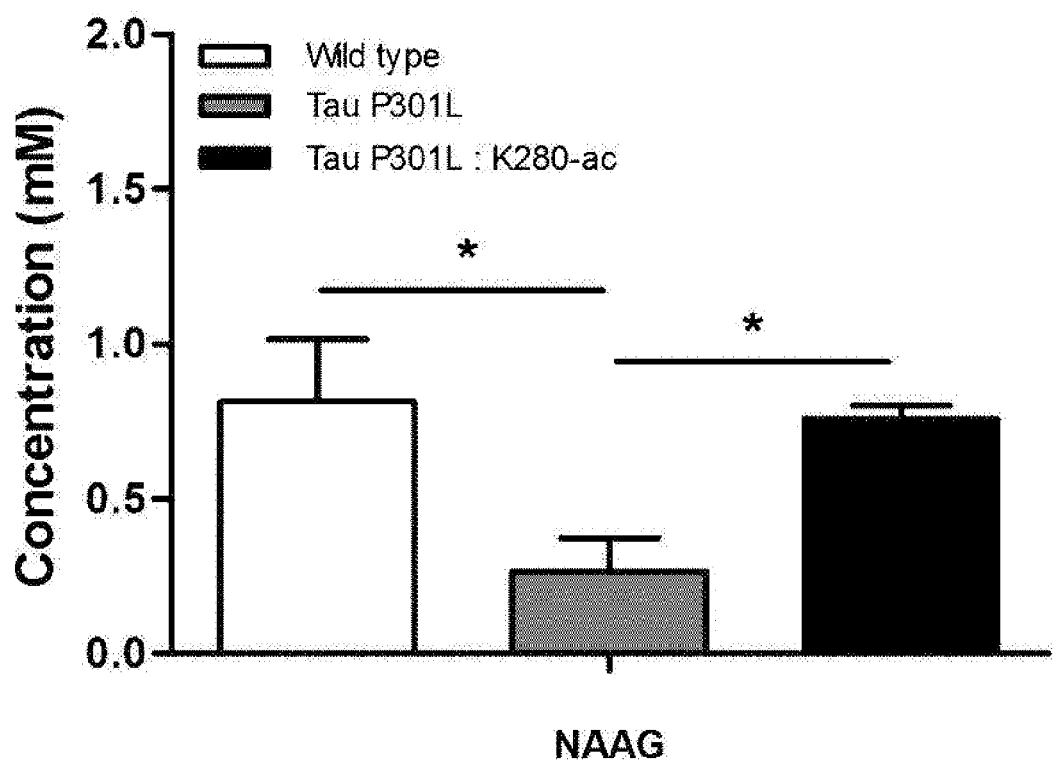

[Fig. 38]
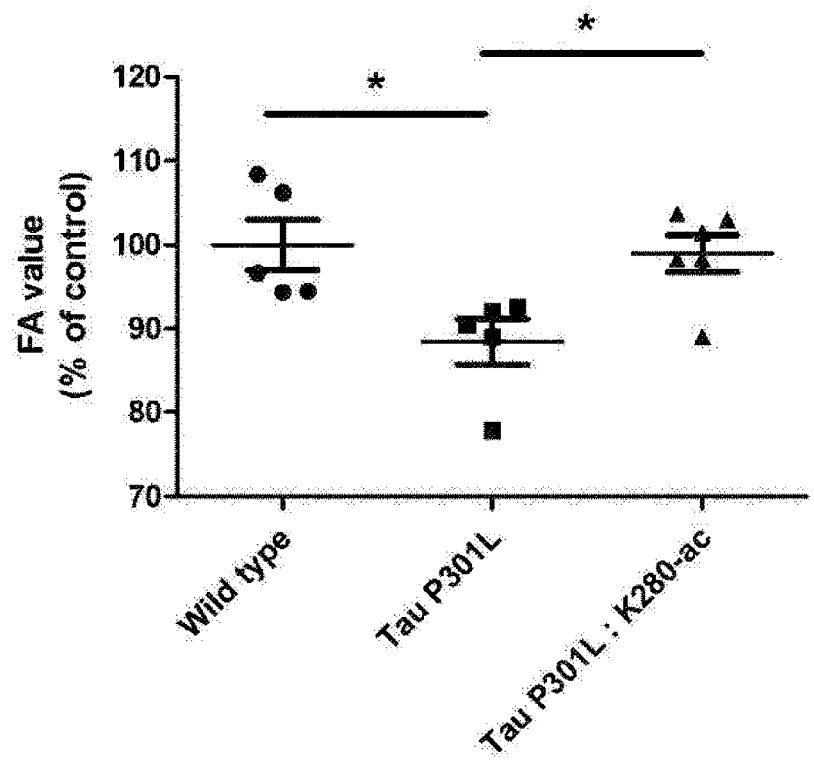
[Fig. 39]
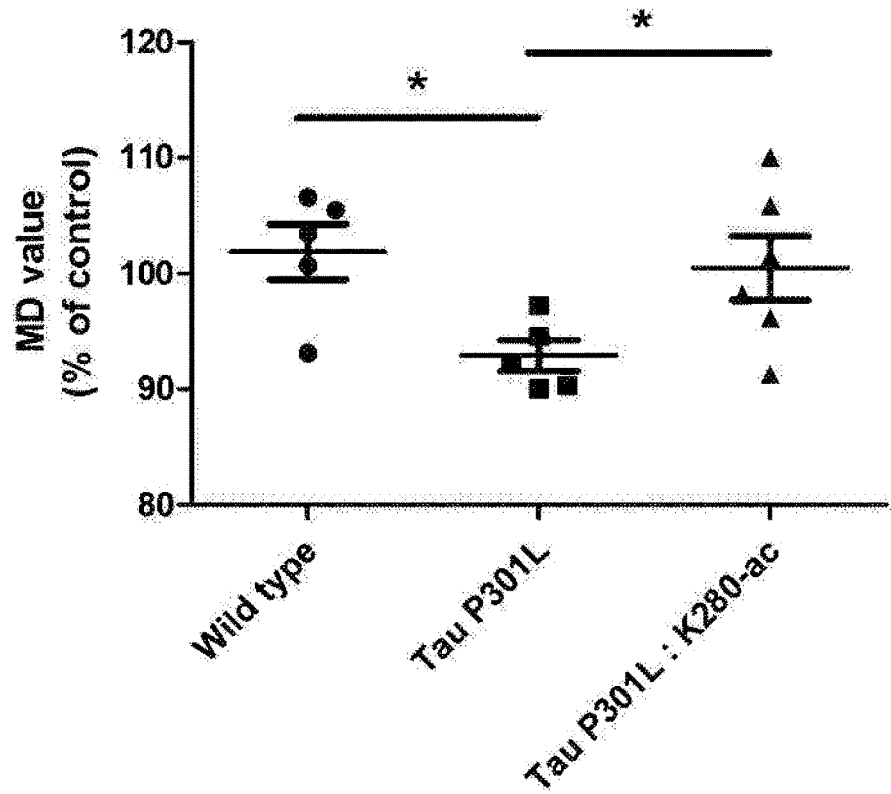

[Fig. 40]
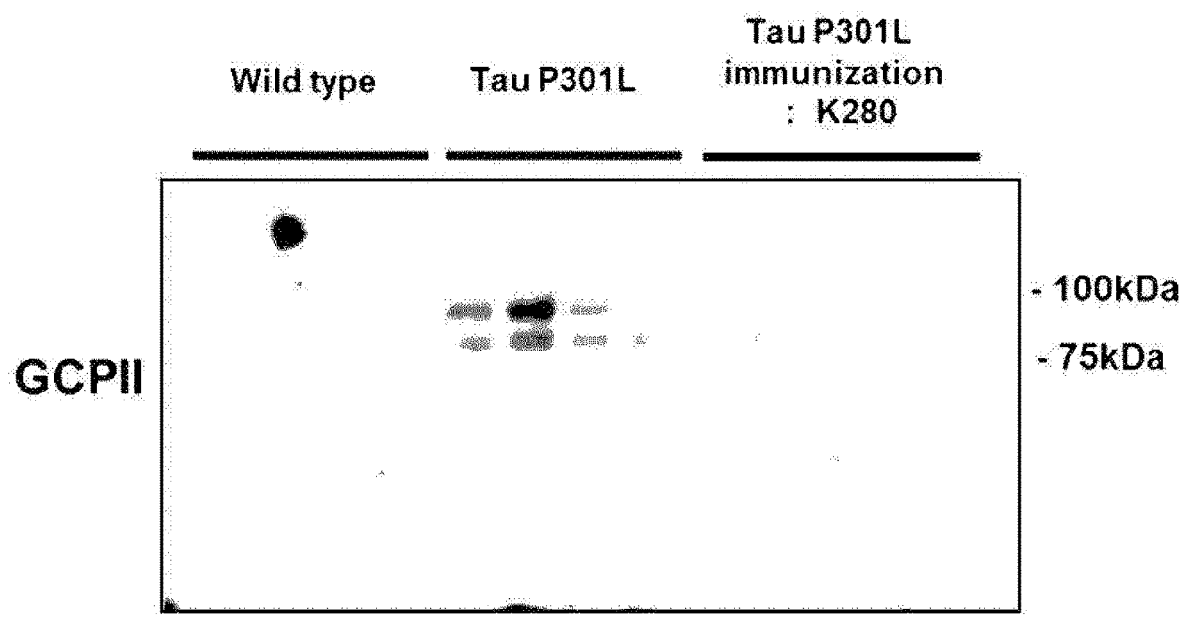

SEQUENCE LISTING

```
<160> NUMBER OF SEQ ID NOS: 6

<210> SEQ ID NO 1
<211> LENGTH: 12
<212> TYPE: PRT
<213> ORGANISM: Artificial Sequence
<220> FEATURE:
<223> OTHER INFORMATION: amino acid sequence for mutated tau protein
      fragment
<220> FEATURE:
<221> NAME/KEY: MOD_RES
<222> LOCATION: (6)
<223> OTHER INFORMATION: ACETYLATOIN,

<400> SEQUENCE: 1

Val Gln Ile Ile Asn Lys Lys Leu Asp Leu Ser Asn
1               5                   10

<210> SEQ ID NO 2
<211> LENGTH: 441
<212> TYPE: PRT
<213> ORGANISM: Homo sapiens

<400> SEQUENCE: 2

Met Ala Glu Pro Arg Gln Glu Phe Glu Val Met Glu Asp His Ala Gly
1               5                   10                  15

Thr Tyr Gly Leu Gly Asp Arg Lys Asp Gln Gly Gly Tyr Thr Met His
                20                  25                  30

Gln Asp Gln Glu Gly Asp Thr Asp Ala Gly Leu Lys Glu Ser Pro Leu
            35                  40                  45

Gln Thr Pro Thr Glu Asp Gly Ser Glu Glu Pro Gly Ser Glu Thr Ser
        50                  55                  60

Asp Ala Lys Ser Thr Pro Thr Ala Glu Asp Val Thr Ala Pro Leu Val
65                  70                  75                  80

Asp Glu Gly Ala Pro Gly Lys Gln Ala Ala Ala Gln Pro His Thr Glu
                85                  90                  95

Ile Pro Glu Gly Thr Thr Ala Glu Glu Ala Gly Ile Gly Asp Thr Pro
            100                 105                 110

Ser Leu Glu Asp Glu Ala Ala Gly His Val Thr Gln Ala Arg Met Val
        115                 120                 125

Ser Lys Ser Lys Asp Gly Thr Gly Ser Asp Asp Lys Lys Ala Lys Gly
    130                 135                 140

Ala Asp Gly Lys Thr Lys Ile Ala Thr Pro Arg Gly Ala Ala Pro Pro
145                 150                 155                 160

Gly Gln Lys Gly Gln Ala Asn Ala Thr Arg Ile Pro Ala Lys Thr Pro
                165                 170                 175

Pro Ala Pro Lys Thr Pro Pro Ser Ser Gly Glu Pro Lys Ser Gly
            180                 185                 190

Asp Arg Ser Gly Tyr Ser Ser Pro Gly Ser Pro Gly Thr Pro Gly Ser
```

```
                    195                 200                 205

Arg Ser Arg Thr Pro Ser Leu Pro Thr Pro Pro Thr Arg Glu Pro Lys
    210                 215                 220

Lys Val Ala Val Val Arg Thr Pro Pro Lys Ser Pro Ser Ser Ala Lys
225                 230                 235                 240

Ser Arg Leu Gln Thr Ala Pro Val Pro Met Pro Asp Leu Lys Asn Val
                245                 250                 255

Lys Ser Lys Ile Gly Ser Thr Glu Asn Leu Lys His Gln Pro Gly Gly
            260                 265                 270

Gly Lys Val Gln Ile Ile Asn Lys Lys Leu Asp Leu Ser Asn Val Gln
        275                 280                 285

Ser Lys Cys Gly Ser Lys Asp Asn Ile Lys His Val Pro Gly Gly Gly
    290                 295                 300

Ser Val Gln Ile Val Tyr Lys Pro Val Asp Leu Ser Lys Val Thr Ser
305                 310                 315                 320

Lys Cys Gly Ser Leu Gly Asn Ile His His Lys Pro Gly Gly Gly Gln
                325                 330                 335

Val Glu Val Lys Ser Glu Lys Leu Asp Phe Lys Asp Arg Val Gln Ser
            340                 345                 350

Lys Ile Gly Ser Leu Asp Asn Ile Thr His Val Pro Gly Gly Gly Asn
        355                 360                 365

Lys Lys Ile Glu Thr His Lys Leu Thr Phe Arg Glu Asn Ala Lys Ala
    370                 375                 380

Lys Thr Asp His Gly Ala Glu Ile Val Tyr Lys Ser Pro Val Val Ser
385                 390                 395                 400

Gly Asp Thr Ser Pro Arg His Leu Ser Asn Val Ser Ser Thr Gly Ser
                405                 410                 415

Ile Asp Met Val Asp Ser Pro Gln Leu Ala Thr Leu Ala Asp Glu Val
            420                 425                 430

Ser Ala Ser Leu Ala Lys Gln Gly Leu
        435                 440

<210> SEQ ID NO 3
<211> LENGTH: 12
<212> TYPE: PRT
<213> ORGANISM: Artificial Sequence
<220> FEATURE:
<223> OTHER INFORMATION: amino acid sequence for tau protein fragment

<400> SEQUENCE: 3

Val Gln Ile Ile Asn Lys Lys Leu Asp Leu Ser Asn
1               5                   10

<210> SEQ ID NO 4
<211> LENGTH: 12
<212> TYPE: PRT
<213> ORGANISM: Artificial Sequence
<220> FEATURE:
<223> OTHER INFORMATION: Amino acid seqeunce for Tau N-terminal fragment

<400> SEQUENCE: 4

Gln Glu Phe Glu Val Met Glu Asp His Ala Gly Thr
1               5                   10

<210> SEQ ID NO 5
<211> LENGTH: 7
<212> TYPE: PRT
<213> ORGANISM: Artificial Sequence
<220> FEATURE:
```

```
<223> OTHER INFORMATION: amino acid sequence for mutated tau protein
      fragment

<400> SEQUENCE: 5

Ile Ile Asn Lys Lys Leu Asp
1               5

<210> SEQ ID NO 6
<211> LENGTH: 7
<212> TYPE: PRT
<213> ORGANISM: Artificial Sequence
<220> FEATURE:
<223> OTHER INFORMATION: amino acid sequence for mutated tau protein
      fragment

<400> SEQUENCE: 6

Ile Asn Lys Lys Leu Asp Leu
1               5
```

MUTATED TAU PROTEIN FRAGMENT AND USE THEREOF

CROSS REFERENCE TO RELATED APPLICATIONS

This application is a National Stage of International Application No. PCT/KR2017/015137 filed Dec. 20, 2017, claiming priority based on Korean Patent Application No. 10-2016-0175705 filed Dec. 21, 2016.

TECHNICAL FIELD

The present invention relates to a modified tau protein fragment and a use thereof. More specifically, the present invention relates to a modified tau protein fragment consisting of 12 amino acids, and a composition for preventing a degenerative neurological disease, comprising the same as an active ingredient.

BACKGROUND ART

Alzheimer's disease, which accounts for about 50% of onset forms of dementia, is a degenerative cranial nerve disease with an increased onset rate since the age of 65, and is rapidly increasing all over the world as the population ages.

It has been believed that accumulation of β-amyloid, hyperphosphorylation of tau protein, or increased β-amyloid production caused by presenilin 1 plays an important role in causes for onset of Alzheimer's disease. Among these, nerve cell toxicity caused by accumulation of β-amyloid has been thought to be a major cause for onset of Alzheimer's dementia (Hardy A J et al., *Science*, 256, 184-185, 1992). However, as a phase III trial for solanezumab which was an Eli Lilly and Company's new drug candidate for Alzheimer's disease failed, it has been found that nerve cell toxicity caused by accumulation of β-amyloid is not remarkable. Therefore, focuses are on the idea that abnormal hyperphosphorylation of tau protein acts as a cause for onset of Alzheimer's disease.

Tau protein is a protein that stabilizes the microtubule which is a protein that transports a cellular material. The tau protein exists in six isoforms in the human body and is abundant in neurons of the central nervous system. In addition, in a case where a mutation occurs in the tau protein, it is known that the tau protein is hyperphosphorylated, which allows neurofibrillary tangles (NFTs) to be abnormally accumulated in nerve cells, thereby causing a degenerative neurological disease such as dementia and Parkinson's disease (Dong Hee Choi et al., *Brain & NeuroRehabilitation*, 4, 21-29, 2011).

However, the human tau protein consisting of 441 amino acids has a wide variety of locations where post-translational modification may occur, which makes it difficult to find, in the tau protein, a target portion that exhibits a preventive or therapeutic effect on dementia. Accordingly, there is a need to develop vaccines or therapeutic agents for a degenerative neurological disease which target the tau protein.

DISCLOSURE OF INVENTION

Technical Problem

Accordingly, the present inventors have studied to develop effective vaccines and therapeutic agents for a degenerative neurological disease. As a result, the present inventors have found that a modified tau protein fragment consisting of 12 amino acids effectively produces a neutralizing antibody and the fragment decreases aggregation of tau proteins. In addition, the present inventors have found that in experiments using a dementia-induced animal model, the animal model into which the fragment has been administered exhibits improved motor ability and cognitive ability, and thus have completed the present invention.

Solution to Problem

In order to solve the above problem, the present invention provides a modified tau protein fragment having a sequence of 12 amino acids.

In addition, the present invention provides a vaccine composition for preventing or treating a degenerative neurological disease, comprising the modified tau protein fragment as an active ingredient.

Furthermore, the present invention provides an antibody or a fragment thereof which binds to the modified tau protein.

In addition, the present invention provides a vector comprising a nucleotide sequence that encodes the antibody or a fragment thereof.

Furthermore, the present invention provides a host cell transformed with the vector.

In addition, the present invention provides a pharmaceutical composition for preventing or treating a degenerative neurological disease, comprising the antibody or a fragment thereof as an active ingredient.

Furthermore, the present invention provides a method for preventing or treating a degenerative neurological disease, comprising a step of administering the vaccine composition to an individual who is expected to develop the degenerative neurological disease or has developed the degenerative neurological disease.

In addition, the present invention provides a method for preventing or treating a degenerative neurological disease, comprising a step of administering the pharmaceutical composition to an individual who is expected to develop the degenerative neurological disease or has developed the degenerative neurological disease.

Furthermore, the present invention provides a pharmaceutical composition for treating depression caused by a degenerative neurological disease, comprising the modified tau protein fragment as an active ingredient.

In addition, the present invention provides a composition for diagnosing a degenerative neurological disease, comprising the antibody or a fragment thereof as an active ingredient.

Furthermore, the present invention provides a diagnostic kit for a degenerative neurological disease, comprising the antibody or a fragment thereof as an active ingredient.

Advantageous Effects of Invention

The modified tau protein fragment of the present invention consists of 12 amino acids, and thus is easily prepared. In addition, in a case where the modified tau protein fragment is injected as an antigen into an individual, a neutralizing antibody against the modified tau protein is produced. In addition, the modified tau protein fragment inhibits aggregation of abnormal tau proteins. Accordingly, the modified tau protein fragment of the present invention can be usefully used for preventing or treating a degenerative neurological disease.

BRIEF DESCRIPTION OF DRAWINGS

FIG. 1 illustrates a view showing the amino acid sequences of modified tau protein fragments prepared in an embodiment of the present invention. In FIG. 1, the sequence VAVVRTPPKSP are the amino acid residues from position 226 to position 236 of SEQ ID NO: 2; the sequence VQIINKKLDLSN is SEQ ID NO: 1; the sequence GGSVQIVYKPVDLS are the amino acid residues from position 303 to position 316 of SEQ ID NO: 2; and the sequence NAKAKTDHGAE are the amino acid residues from position 381 to position 391 of SEQ ID NOL 2.

FIG. 2 illustrates a view obtained by identifying, through western blotting, expression levels of the entire tau protein and a tau protein in which the 280$^{th}$ amino acid is acetylated, over time, in Tau-P30IL dementia mice.

FIG. 3 illustrates graphs showing the expression levels of the entire tau protein and the tau protein in which the 280$^{th}$ amino acid is acetylated, over time, in the Tau-P30IL dementia mice.

FIG. 4 illustrates photographs showing, through immunohistochemical staining, the expression level of the tau protein in which the 280$^{th}$ amino acid is acetylated, over time, in the Tau-P30IL dementia mice.

FIG. 5 illustrates a graph showing the expression level of the tau protein in which the 280$^{th}$ amino acid is acetylated, over time, in the Tau-P30IL dementia mice.

FIG. 6a illustrates a view obtained by identifying whether after K280-ac fragment was administered into Tau-P301L dementia mice, an antibody against the same was generated.

FIG. 6b illustrates a view obtained by identifying whether after pT231 fragment was administered into Tau-P301L dementia mice, an antibody against the same was generated.

FIG. 6c illustrates a view obtained by identifying whether after Glu391 fragment was administered into Tau-P301L dementia mice, an antibody against the same was generated.

FIG. 6d illustrates a view obtained by identifying whether after K311ac fragment was administered into Tau-P301L dementia mice, an antibody against the same was generated.

FIG. 6e illustrates views obtained by identifying whether after the entire tau fragment was administered into Tau-P301L dementia mice, an antibody against the same was generated. In FIG. 6e, the sequence GAEIVYKSPVV are the amino acid residues from position 389 to position 399 of SEQ ID NO: 2; the sequence IVYKSPVVSGD are the amino acid residues from position 392 to position 402 of SEQ ID NO: 2; the sequence NAKAKTDHGAE (twice) are the amino acid residues from position 381 to position 391 of SEQ ID NO: 2.

FIG. 7 illustrates a view obtained by identifying, through a fear conditioning experiment, a behavior-improving effect in the dementia mice following administration of the K280-ac fragment. In FIG. 7, the legend "Tau-P301L: VQIVYK-ac" represents the amino acid residues from position 303 to position 316 of SEQ ID NO: 2 wherein the amino acid residues VQIVYK at positions 306-311 of SEQ ID NO: 2 are acetylated.

FIG. 8 illustrates a view obtained by identifying, through a strength test experiment, a behavior-improving effect in the dementia mice following administration of the K280-ac fragment. In FIG. 8, the legend "Tau P301L: VQIVYK-ac" represents the amino acid residues from position 303 to position 316 of SEQ ID NO: 2 wherein the amino acid residues VQIVYK at positions 306-311 of SEQ ID NO: 2 are acetylated.

FIG. 9 illustrates a view obtained by identifying, through a vertical test experiment, a behavior-improving effect in the dementia mice following administration of the K280-ac fragment. In FIG. 9, the legend "Tau P301L: VQIVYK-ac" represents the amino acid residues from position 303 to position 316 of SEQ ID NO: 2 wherein the amino acid residues VQIVYK at positions 306-311 of SEQ ID NO: 2 are acetylated.

FIG. 10 illustrates a view obtained by identifying, through a water maze experiment, a behavior-improving effect in the dementia mice following administration of the K280-ac fragment. In FIG. 10, the legend "Tau P301L: VQIVYK-ac" represents the amino acid residues from position 303 to position 316 of SEQ ID NO: 2 wherein the amino acid residues VQIVYK at positions 306-311 of SEQ ID NO: 2 are acetylated.

FIG. 11 illustrates views obtained by comparing antibody production after primary and secondary administration, as a vaccine, of a tau protein N-terminal fragment or the K280-ac fragment of the tau protein.

FIG. 12 illustrates photographs obtained by identifying, through a nest building test experiment, a behavior-improving effect in the dementia mice following administration of the K280-ac fragment.

FIG. 13 illustrates a graph in which the behavior-improving effect identified, through the nest building test experiment, in the dementia mice following administration of the K280-ac fragment is expressed as a score.

FIG. 14 illustrates a view showing a training pattern (sec) for Tau-P301L-K280-ac dementia mice and normal mice.

FIG. 15 illustrates a view showing a training pattern (rpm) for the Tau-P301L-K280-ac dementia mice and the normal mice.

FIG. 16 illustrates a graph in which a behavior-improving effect in the dementia mice following administration of the K280-ac fragment is measured in terms of time through a rota-rod test experiment and the measured time is expressed as a score.

FIG. 17 illustrates a graph in which a behavior-improving effect in the dementia mice following administration of the K280-ac fragment is measured in terms of rpm through a rota-rod test experiment and the measured rpm is expressed as a score.

FIG. 18 illustrates a view obtained by identifying, through a Y-maze experiment, a behavior-improving effect in the dementia mice following administration of the K280-ac fragment.

FIG. 19 illustrates views obtained by identifying, through a novel object recognition experiment, a behavior-improving effect in the dementia mice following administration of the K280-ac fragment.

FIG. 20 illustrates a view obtained by measuring, through a forced swimming test experiment, immobility in the dementia mice following administration of the K280-ac fragment, and identifying a depression-ameliorating effect of the fragment.

FIG. 21 illustrates a view obtained by measuring, through a forced swimming test experiment, swimming in the dementia mice following administration of the K280-ac fragment, and identifying a depression-ameliorating effect of the fragment.

FIG. 22 illustrates a view obtained by measuring, through a forced swimming test experiment, climbing in the dementia mice following administration of the K280-ac fragment, and identifying a depression-ameliorating effect of the fragment.

FIG. 23 illustrates a view obtained by identifying a decreasing effect of the entire tau protein (Tau 5), phosphorylated tau proteins (pSer396, pThr231), and an acetylated tau protein (Ace-K280) are decreased in brain tissues of normal mice, Tau-P301L dementia mice, and Tau-P301L-K280-ac dementia mice.

FIG. 24 illustrates views, each of which shows a proportion of the phosphorylated tau protein (pThr231) or the acetylated tau protein (Ace-K280) relative to the entire tau protein (Tau 5), in brain tissues of normal mice, Tau-P301L dementia mice, and Tau-P301L-K280-ac dementia mice.

FIG. 25 illustrates photographs obtained by extracting brain tissues of normal mice, Tau-P301L dementia mice, and Tau-P301L-K280-ac dementia mice, performing immunohistochemical staining, and identifying expressed levels of the entire tau protein (Tau 5) and the phosphorylated tau protein (pThr231).

FIG. 26 illustrates results obtained by extracting brain tissues of normal mice, Tau-P301L dementia mice, and Tau-P301L-K280-ac dementia mice, performing immunohistochemical staining, and graphically representing the expressed levels of the entire tau protein (Tau 5) and the phosphorylated tau protein (pThr231).

FIG. 27 illustrates photographs obtained by extracting brain tissues of normal mice, Tau-P301L dementia mice, and Tau-P301L-K280-ac dementia mice, and then identifying, through western blotting of cerebral cortical fractions (soluble), expressed levels of the entire tau protein (Tau 5), the phosphorylated tau proteins (pSer396, pThr231), and the acetylated tau protein (Ace-K280), in order to identify changes in aggregated tau proteins following administration of the K280-ac fragment.

FIG. 28 illustrates photographs obtained by extracting brain tissues of normal mice, Tau-P301L dementia mice, and Tau-P301L-K280-ac dementia mice, and then identifying, through western blotting of cerebral cortical fractions (insoluble), expressed levels of the entire tau protein (Tau 5), the phosphorylated tau proteins (pSer396, pThr231), and the acetylated tau protein (Ace-K280), in order to identify changes in aggregated tau proteins following administration of the K280-ac fragment.

FIG. 29 illustrates photographs obtained by extracting brain tissues of normal mice, Tau-P301L dementia mice, and Tau-P301L-K280-ac dementia mice, and then identifying, through western blotting, expressed levels of synapse-related proteins, in order to identify a synapse-improving effect following administration of the K280-ac fragment.

FIG. 30 illustrates a graph obtained by extracting brain tissues of normal mice, Tau-P301L dementia mice, and Tau-P301L-K280-ac dementia mice, and then identifying, through qPCR, an expressed level of IFN-γ which is an inflammation-related gene, in order to identify an inflammation-improving effect following administration of the K280-ac fragment.

FIG. 31 illustrates a graph obtained by extracting brain tissues of normal mice, Tau-P301L dementia mice, and Tau-P301L-K280-ac dementia mice, and then identifying, through qPCR, an expressed level of IL-12 which is an inflammation-related gene, in order to identify an inflammation-improving effect following administration of the K280-ac fragment.

FIG. 32 illustrates a graph obtained by extracting brain tissues of normal mice, Tau-P301L dementia mice, and Tau-P301L-K280-ac dementia mice, and then identifying, through qPCR, an expressed level of IL-4 which is an inflammation-related gene, in order to identify an inflammation-improving effect following administration of the K280-ac fragment.

FIG. 33 illustrates a graph obtained by extracting brain tissues of normal mice, Tau-P301L dementia mice, and Tau-P301L-K280-ac dementia mice, and then identifying, through qPCR, an expressed level of IL-22 which is an inflammation-related gene, in order to identify an inflammation-improving effect following administration of the K280-ac fragment.

FIG. 34 illustrates photographs obtained by extracting brain tissues of normal mice, Tau-P301L dementia mice, and Tau-P301L-K280-ac dementia mice, and then performing identification through immunohistochemical staining, in order to identify distribution, in the brain tissues, of antibodies produced by administration of the K280-ac fragment.

FIG. 35 illustrates a view obtained by extracting brain tissues of normal mice, Tau-P301L dementia mice, and Tau-P301L-K280-ac dementia mice, and then performing identification through western blotting, in order to identify distribution, in the brain tissues, of antibodies produced by administration of the K280-ac fragment.

FIG. 36 illustrates a photograph obtained by designating, as a region of interest (ROI), the hippocampuses of normal mice, Tau-P301L dementia mice, and Tau-P301L-K280-ac dementia mice, and performing MR spectroscopy (MRS), in order to identify a metabolic imaging index-improving effect following administration of the K280-ac fragment.

FIG. 37 illustrates a graph showing concentrations of N-acetyl-aspartyl-glutamic acid (NAAG) in normal mice, Tau-P301L dementia mice, and Tau-P301L-K280-ac dementia mice, in order to identify a metabolic imaging index-improving effect following administration of the K280-ac fragment.

FIG. 38 illustrates a graph showing fractional anisotropy (FA) values in normal mice, Tau-P301L dementia mice, and Tau-P301L-K280-ac dementia mice, in order to identify a metabolic imaging index-improving effect following administration of the K280-ac fragment.

FIG. 39 illustrates a graph showing mean diffusivity (MD) values in normal mice, Tau-P301L dementia mice, and Tau-P301L-K280-ac dementia mice, in order to identify a metabolic imaging index-improving effect following administration of the K280-ac fragment.

FIG. 40 illustrates a view obtained by measuring expressed levels of GCP-II in normal mice, Tau-P301L dementia mice, and Tau-P301L-K280-ac dementia mice, in order to identify a GCP-II-decreasing effect following administration of the K280-ac fragment.

DETAILED DESCRIPTION OF INVENTION

Hereinafter, the present invention will be described in detail.

The present invention provides a modified tau protein fragment having the following sequence of 12 amino acids:

```
                                              (SEQ ID NO: 1)
Val-Gln-Ile-Ile-Asn-Lys-Lys-Leu-Asp-Leu-Ser-Asn
```

The sequence is characterized in that lysine, the $6^{th}$ amino acid, is acetylated.

In addition, the modified tau protein fragment may be a modified tau protein fragment having a sequence of 7 amino acids such as Ile-Ile-Asn-Lys-Lys-Leu-Asp (SEQ ID NO: 5) which is a sequence of the $277^{th}$ to $283^{rd}$ amino acids in the amino acid sequence of the tau protein represented by SEQ ID NO: 2 in which the $280^{th}$ amino acid is acetylated, or Ile-Asn-Lys-Lys-Leu-Asp-Leu (SEQ ID NO: 6) which is a sequence of the $278^{th}$ to $284^{th}$ amino acids in the amino acid sequence of the tau protein represented by SEQ ID NO: 2 in which the 280$^{th}$ amino acid is acetylated.

The term "tau protein" as used herein means a protein that consists of 441 amino acids and stabilizes the microtubule which is a protein that transports a cellular material. In a case where a mutation occurs in the tau protein, the tau protein is hyperphosphorylated, which allows neurofibrillary tangles (NFTs) to be abnormally accumulated in nerve cells, thereby causing a degenerative neurological disease such as Alzheimer's disease and Parkinson's disease.

The modified tau protein fragment may be easily prepared by a known technique for preparing a protein. In addition, the modified tau protein fragment may be prepared by acetylating the 280$^{th}$ amino acid in the full-length tau protein having the amino acid sequence represented by SEQ ID NO: 2, and then performing treatment with a suitable restriction enzyme so that a fragment having a sequence of the 275$^{th}$ to 286$^{th}$ amino acids is obtained. In addition, the modified tau protein fragment may be prepared by preparing a tau protein fragment having the amino acid sequence represented by SEQ ID NO: 3, and then acetylating the 6$^{th}$ amino acid. However, the present invention is not limited thereto.

Specifically, the modified tau protein fragment may be prepared through a preparation method that includes a step of transforming a host cell with an expression vector which contains a gene encoding the amino acid sequence represented by SEQ ID NO: 3; a step of culturing the transformed host cell; a step of obtaining a tau protein fragment from a culture; and a step of acetylating lysine, the 6$^{th}$ amino acid, in the obtained tau protein fragment.

The host cell may be a prokaryotic or eukaryotic cell. Specifically, the prokaryotic cell may be E. coli or yeast. The eukaryotic cell may be an NS/0 myeloma cell, a 293 cell, a Chinese hamster ovary cell (CHO cell), a HeLa cell, a CapT cell (human amniotic fluid-derived cell), or a COS cell.

The transformation may be carried out by transient transfection, microinjection, transduction, cell fusion, calcium phosphate precipitation, liposome-mediated transfection, DEAE dextran-mediated transfection, polybrene-mediated transfection, electroporation, or gene gun.

The present invention provides a vaccine composition for preventing or treating a degenerative neurological disease, comprising, as an active ingredient, the modified tau protein fragment of the present invention.

The degenerative neurological disease may be a tau protein-mediated neurological disease. Specifically, the tau protein-mediated neurological disease may be Alzheimer's disease or Parkinson's disease.

Specifically, the tau protein-mediated neurological disease (tauopathy) may be primary age-related tauopathy, chronic traumatic encephalopathy, progressive supranuclear palsy, corticobasal degeneration, frontotemporal dementia, Lytico-Bodig disease, Parkinsonism, subacute sclerosing meningitis, lead encephalopathy, tuberous sclerosis, ganglioglioma, gangliocytoma, meningioangiomatosis, subacute sclerosing panencephalitis, Hallervorden-Spatz disease, or lipofuscinosis.

In addition, the tauopathy may be Alzheimer's disease (AD), Pick's disease (PiD), a group of related disorders collectively referred to as frontotemporal dementia (FTDP-17) with Parkinsonism linked to chromosome 17, amyotrophic lateral sclerosis (ALS), Creutzfeld-Jakob disease (CJD), boxer dementia (DP), Gerstmann-Sträussler-Scheinker disease (GSSD), Lewy body disease, chronic traumatic encephalopathy (CTE), spinal cord injury, epilepsy, or Huntington's disease.

The vaccine composition may further comprise one or more selected from the group consisting of pharmaceutically acceptable carriers, diluents, and adjuvants. Suitable carriers for vaccines are known to those skilled in the art and may include, but are not limited to, proteins, sugars, and the like. The carriers may be aqueous or non-aqueous solutions, suspensions, and emulsions. Examples of carriers which are non-aqueous solutions may include propylene glycol, polyethylene glycol, vegetable oil such as olive oil, and injectable organic ester such as ethyl oleate.

Examples of carriers which are aqueous solutions may include water, an alcohol/aqueous solution, an emulsion, or a suspension which includes saline and buffered media. Examples of carriers for parental administration may include a sodium chloride solution, Ringer's dextrose, dextrose and sodium chloride, lactated Ringer, or fixed oil. Examples of carriers for intravenous injection may include an electrolyte supplement such as one based on Ringer's dextrose, a liquid, and a nutritional supplement. Preservatives and other additives such as antimicrobial agents, antioxidants, chelating agents, and inert gases may be additionally present. Preferred preservatives may include formalin, thimerosal, neomycin, polymyxin B, and amphotericin B.

In addition, the vaccine composition may further comprise an adjuvant (an immunomodulatory agent or an immunopotentiating agent). The adjuvant refers to a compound or mixture which enhances an immune response and/or accelerates an absorption rate after inoculation, and may include any absorption accelerator. Acceptable adjuvants may include, but are not limited to, Freund's complete adjuvant, Freund's incomplete adjuvant, saponin, a mineral gel such as aluminum hydroxide, a surfactant such as lysolecithin, pluronic polyol, polyanions, a peptide, oil or a hydrocarbon emulsion, keyhole limpet hemocyanin, dinitrophenol, and the like.

The vaccine composition may be administered through any one route of administration selected from the group consisting of transdermal, intramuscular, intraperitoneal, intravenous, subcutaneous, and nasal routes of administration, and is preferably administered by injection.

The vaccine composition is administered in a pharmaceutically effective amount. The term "pharmaceutically effective amount" as used herein means an amount which is sufficient to enable the vaccine composition to exhibit a vaccine effect without causing side effects or serious or excessive immune responses. A level of the effective amount may vary depending on various factors including a disorder to be treated, severity of the disorder, activity of a specific compound, route of administration, a rate at which the protein is removed, duration of treatment, drugs used in combination or simultaneously with the protein, the individual's age, weight, sex, dietary habit, general health condition, and factors known in the medical field. Various general issues to be considered at the time of determining a "therapeutically effective amount" are known to those skilled in the art, and are described, for example, in Gilman et al., eds., Goodman And Gilman's: The Pharmacological Bases of Therapeutics, 8th ed., Pergamon Press, 1990; and Remington's Pharmaceutical Sciences, 17th ed., Mack Publishing Co., Easton, Pa., 1990.

A dose of the vaccine composition is desirably determined in consideration of the patient's age, sex, condition, a degree of absorption of its active ingredient in the body, an inactivation rate, and drugs used in combination. The vaccine composition may be administered in an amount of 0.0001 mg/kg (body weight) to 100 mg/kg (body weight) based on the modified tau protein fragment.

The present invention provides an antibody or a fragment thereof which binds to the modified tau protein fragment of the present invention.

The term "antibody" as used herein means an immune protein that binds to an antigen and interferes with an action of the antigen or eliminates the antigen. There are five types of antibodies, IgM, IgD, IgG, IgA, and IgE, and these antibodies contain heavy chains produced by heavy chain constant region genes, μ, δ, γ, α, and ε, respectively. In antibody technology, IgG is mainly used. IgG has four isotypes, IgG1, IgG2, IgG3, and IgG4, each of which may be different in terms of structural and functional characteristics.

The IgG forms a Y-shaped, highly stable structure (molecular weight: about 150 kDa) made up of two heavy chain (about 50 kDa) proteins and two light chain (about 25 kDa) proteins. In antibodies, light and heavy chains are divided into a variable region of which an amino acid sequence differs from one antibody to another, and a constant region of which an amino acid sequence is the same among antibodies. There are CH1, H (hinge), CH2, and CH3 domains in the heavy chain constant region. Each of the domains is composed of two β-sheets, and the domains are connected to each other via an intramolecular disulfide bond. Two variable regions of heavy and light chains are combined to form an antigen binding site. For the site, there is one each on two Y-shaped arms. Such a portion capable of binding to an antigen is called Fab (antibody binding fragment) and a portion that does not bind to an antigen is called Fc (crystallizable fragment). Fab and Fc are connected to each other via a flexible hinge region.

The term "CDR" as used herein means a hypervariable region that is a site which is in heavy chain and light chain variable regions of an antibody and of which an amino acid sequence differs from one antibody from another, wherein the site binds to an antigen. Taking a look at a stereostructure of an antibody, CDR has a loop shape on a surface of the antibody; and under the loop, a framework region (FR) exists for structurally supporting CDR. There are three loop structures in each of the heavy chain and the light chain, and these six regional loop structures are combined together to directly contact an antigen.

In addition, the antibody fragment may be any one selected from the group consisting of Fab, scFv, F(ab)$_2$, and Fv. The antibody fragments refer to antigen binding domains except for a crystallizable region (Fc region) which has a function (effector function) to transmit stimulus caused by binding with an antigen to a cell, a complement, or the like, and may include $3^{rd}$ generation antibody fragments such as a single domain antibody and a minibody.

In addition, the antibody fragment has advantages of having a good penetration rate into tissues and tumors due to its smaller size than IgG of a complete structure, and having low production cost due to the fact that it can be produced in bacteria. In addition, since the antibody fragment lacks Fc, the antibody fragment is used in a case where a function to transmit stimulus caused by binding with an antigen to a cell, a complement, or the like is not desired. The antibody fragment is suitable for diagnosis in the body due to its short half-life in the human body. However, in a case where among amino acids constituting an antibody, some basic, acidic, or neutral amino acids are replaced with each other, an isoelectric point (pI) intrinsic to the antibody itself may change. Such change in isoelectric point of the antibody may lead changes such as decreased toxic side effects in vivo of the antibody or increased water solubility.

Therefore, in a case of a therapeutic antibody, in consideration of its affinity or structural form, IgG of a complete structure may be used.

The antibody may be easily prepared by a known technique for preparing a monoclonal antibody. A method for preparing a monoclonal antibody may be performed by preparing a hybridoma using B lymphocytes from an immunized animal, or by using a phage display technique. However, the method is not limited thereto.

The present invention provides a vector comprising a nucleotide sequence that encodes the antibody of the present invention or a fragment thereof.

The present invention provides a host cell transformed with the vector of the present invention.

The host cell may be a prokaryotic or eukaryotic cell. Specifically, the prokaryotic cell may be *E. coli* or yeast. The eukaryotic cell may be an NS/0 myeloma cell, a 293 cell, a Chinese hamster ovary cell (CHO cell), a HeLa cell, a CapT cell (human amniotic fluid-derived cell), or a COS cell.

The transformation may be carried out by transient transfection, microinjection, transduction, cell fusion, calcium phosphate precipitation, liposome-mediated transfection, DEAE dextran-mediated transfection, polybrene-mediated transfection, electroporation, or gene gun.

The present invention provides a pharmaceutical composition for preventing or treating a degenerative neurological disease, comprising, as an active ingredient, the antibody of the present invention or a fragment thereof.

Specifically, the tau protein-mediated neurological disease (tauopathy) may be primary age-related tauopathy, chronic traumatic encephalopathy, progressive supranuclear palsy, corticobasal degeneration, frontotemporal dementia, Lytico-Bodig disease, Parkinsonism, subacute sclerosing meningitis, lead encephalopathy, tuberous sclerosis, ganglioglioma, gangliocytoma, meningioangiomatosis, subacute sclerosing panencephalitis, Hallervorden-Spatz disease, or lipofuscinosis.

In addition, the tauopathy may be Alzheimer's disease (AD), Pick's disease (PiD), a group of related disorders collectively referred to as frontotemporal dementia (FTDP-17) with Parkinsonism linked to chromosome 17, amyotrophic lateral sclerosis (ALS), Creutzfeld-Jakob disease (CJD), boxer dementia (DP), Gerstmann-Sträussler-Scheinker disease (GSSD), Lewy body disease, chronic traumatic encephalopathy (CTE), spinal cord injury, epilepsy, or Huntington's disease. The pharmaceutical composition may further comprise one or more selected from the group consisting of pharmaceutically acceptable carriers, diluents, and adjuvants. Suitable carriers for vaccines are known to those skilled in the art and may include, but are not limited to, proteins, sugars, and the like. The carriers may be aqueous or non-aqueous solutions, suspensions, and emulsions. Examples of carriers which are non-aqueous solutions may include propylene glycol, polyethylene glycol, vegetable oil such as olive oil, and injectable organic ester such as ethyl oleate.

Examples of carriers which are aqueous solutions may include water, an alcohol/aqueous solution, an emulsion, or a suspension which includes saline and buffered media. Examples of carriers for parental administration may include a sodium chloride solution, Ringer's dextrose, dextrose and sodium chloride, lactated Ringer, or fixed oil. Examples of carriers for intravenous injection may include an electrolyte supplement such as one based on Ringer's dextrose, a liquid, and a nutritional supplement. Preservatives and other additives such as antimicrobial agents, antioxidants, chelating agents, and inert gases may be additionally present. Preferred preservatives may include formalin, thimerosal, neomycin, polymyxin B, and amphotericin B.

In addition, the pharmaceutical composition may further comprise an adjuvant (an immunomodulatory agent or an immunopotentiating agent). The adjuvant refers to a compound or mixture which enhances an immune response and/or accelerates an absorption rate after inoculation, and may include any absorption accelerator. Acceptable adjuvants may include, but are not limited to, Freund's complete adjuvant, Freund's incomplete adjuvant, saponin, a mineral gel such as aluminum hydroxide, a surfactant such as lysolecithin, pluronic polyol, polyanions, a peptide, oil or a hydrocarbon emulsion, keyhole limpet hemocyanin, dinitrophenol, and the like.

The pharmaceutical composition may be administered through any one route of administration selected from the group consisting of transdermal, intramuscular, intraperitoneal, intravenous, subcutaneous, and nasal routes of administration, and is preferably administered by injection.

The pharmaceutical composition is administered in a pharmaceutically effective amount. The term "pharmaceutically effective amount" as used herein means an amount which is sufficient to enable the pharmaceutical composition to exhibit a vaccine effect without causing side effects or serious or excessive immune responses. A level of the effective amount may vary depending on various factors including a disorder to be treated, severity of the disorder, activity of a specific compound, route of administration, a rate at which the protein is removed, duration of treatment, drugs used in combination or simultaneously with the protein, the individual's age, weight, sex, dietary habit, general health condition, and factors known in the medical field.

A dose of the pharmaceutical composition is desirably determined in consideration of the patient's age, sex, condition, a degree of absorption of its active ingredient in the body, an inactivation rate, and drugs used in combination. The pharmaceutical composition may be administered in an amount of 0.0001 mg/kg (body weight) to 100 mg/kg (body weight) based on the antibody or a fragment thereof.

The present invention provides a method for preventing or treating a degenerative neurological disease, comprising a step of administering the vaccine composition or pharmaceutical composition of the present invention to an individual who is expected to develop the degenerative neurological disease or has developed the degenerative neurological disease.

The present invention provides a pharmaceutical composition for treating depression caused by a degenerative neurological disease, comprising, as an active ingredient, the modified tau protein fragment of the present invention.

The present invention provides a composition for diagnosing a degenerative neurological disease, comprising an agent for detecting a modified tau protein or a gene encoding the modified tau protein.

The detecting agent may be an antibody that binds to the modified tau protein. The antibody is as described above.

In a case where the antibody is used, assays for identifying an amount of the modified tau protein that binds thereto include, but are not limited to, western blotting, enzyme linked immunosorbent assay (ELISA), radioimmunoassay (RIA), radioimmunodiffusion, Ouchterlony immunodiffusion, rocket immunoelectrophoresis, immunohistological staining, immunoprecipitation assay, complement fixation assay, fluorescence activated cell sorter (FACS), protein chip method, and the like.

In addition, the detecting agent may be a primer or probe capable of complementarily binding to the gene encoding the modified tau protein. The primer or probe may be a nucleotide sequence having 10 to 25 consecutive bases which complimentarily binds, in a direction from 5'-end to 3'-end, to a nucleotide sequence of the modified tau protein.

In addition, primers or probes which specifically bind to the modified tau protein may be used for methods such as RT-PCR, competitive RT-PCR, real-time RT-PCR, RNase protection assay (RPA), northern blotting, and gene chip assay.

The term "primer" as used herein means a short nucleic acid sequence having a free 3' hydroxyl group, which can form base pairs with a complementary template and functions as a starting point for copying a template strand. The primer can initiate DNA synthesis in the presence of a reagent for polymerization and four different nucleoside triphosphates in an appropriate buffer solution and at an appropriate temperature. At this time, the reagent for polymerization may be a DNA polymerase or a reverse transcriptase.

As used herein, the term "probe" means a nucleic acid fragment such as RNA or DNA which can form specific binding with a gene or mRNA and corresponds to a few bases in a case of a short probe to hundreds of bases in a case of a long probe. Such a probe may be produced in the form of an oligonucleotide probe, a single-stranded DNA probe, a double-stranded DNA probe, an RNA probe, or the like, and may be labeled for easier detection. However, the present invention is not limited thereto.

The primer or probe of the present invention may be chemically synthesized using a phosphoramidite solid support method, or other well-known methods. Such a nucleic acid may also be modified using many measures known in the art. Examples of such modifications may include methylation, capping, substitution of natural nucleotides with at least one homologue, and internucleotide modification.

In addition, the nucleic acid sequence of the present invention may be modified using a label that can directly or indirectly provide a detectable signal. The label may be a radioisotope label, a fluorescent molecular label, or a biotin label.

The degenerative neurological disease is as described above in the vaccine composition or the pharmaceutical composition.

The present invention provides a diagnostic kit for a degenerative neurological disease, comprising the composition for diagnosing a degenerative neurological disease of the present invention.

The kit can be used to measure an mRNA or protein expression level of a modified tau protein from a sample of an individual, so as to diagnose a degenerative neurological disease. In addition, a primer or probe and an antibody for measuring an mRNA or protein level of the modified tau protein, as well as a composition, solution, or device which includes one or more other constitutents and is suitable for an assay method may be included therein.

Specifically, the diagnostic kit for a degenerative neurological disease of the present invention may include essential elements necessary for carrying out RT-PCR. The RT-PCR kit may include, in addition to respective primer pairs specific for the modified tau protein gene, a test tube or another appropriate container, a reaction buffer, deoxynucleotides (dNTPs), enzymes such as Taq-polymerase and reverse transcriptase, DNAse, RNAse inhibitor, sterile water, and the like. In addition, the RT-PCR kit may include a primer pair specific for a gene used as a quantitative control.

The present invention provides a method for providing information on a degenerative neurological disease, the method comprising i) a step of measuring an expression level of a modified tau protein, in which the $280^{th}$ amino acid is acetylated, in a sample isolated from an individual suspected of having a degenerative neurological disease; ii) a step of comparing the expression level of the modified tau protein with an expression level of the modified tau protein in a normal control sample; and iii) a step of determining that in a case where the expression level of the modified tau protein is higher than that in the control, the individual has a high probability of developing the degenerative neurological disease.

A procedure of isolating a sample from an individual may be carried out using a known process. The term "sample" as used herein includes, but is not limited to, a sample such as a tissue, a cell, blood, and plasma, which has a different mRNA or protein expression level of the modified tau protein, and the like.

The step of measuring mRNA may be carried out using reverse transcriptase polymerase chain reaction (RT-PCR), competitive RT-PCR, real-time quantitative RT-PCR, RNase protection assay, northern blotting, and gene chip assay. However, the present invention is not limited thereto.

In addition, the step of measuring the protein may be carried out by western blotting, ELISA, radioimmunoassay, radioimmunodiffusion, Ouchterlony immunodiffusion, rocket immunoelectrophoresis, immunohistological staining, immunoprecipitation assay, complement fixation assay, FACS, or protein chip method. However, the present invention is not limited thereto.

Through the above assay methods, it is possible to compare an amount of an antigen-antibody complex formed in the normal control with an amount of an antigen-antibody complex formed in the individual, and to determine whether the individual has been exposed to ozone by determining whether an expression level from a gene to a protein is significantly increased or decreased.

The term "antigen-antibody complex" as used herein means a conjugate of a modified tau protein with an antibody specific thereto, and an amount of the antigen-antibody complex formed can be quantitatively measured through a signal size of a detection label. Such a detection label may be selected from the group consisting of enzymes, fluorescent substances, ligands, luminescent substances, microparticles, redox molecules, and radioisotopes, but is not necessarily limited thereto. In a case where an enzyme is used as the detection label, available enzymes include β-glucuronidase, β-D-glucosidase, β-D-galactosidase, urease, peroxidase, alkaline phosphatase, and the like. The ligands include, but are not limited to, biotin derivatives, and the like.

The present invention provides a use of the vaccine composition of the present invention for preventing or treating a degenerative neurological disease.

In addition, the present invention provides a use of the pharmaceutical composition of the present invention for preventing or treating a degenerative neurological disease.

Furthermore, the present invention provides a use of the vaccine composition of the present invention for the manufacture of a medicament for preventing or treating a degenerative neurological disease.

In addition, the present invention provides a use of the pharmaceutical composition of the present invention for the manufacture of a medicament for preventing or treating a degenerative neurological disease.

MODE FOR THE INVENTION

Hereinafter, the present invention will be described in detail by way of the following examples. However, the following examples are intended to only illustrate the present invention, and the present invention is not limited thereby.

I. Preparation of Modified Tau Protein Fragments and Antibodies Thereagainst

Preparation Example 1. Preparation of Modified Tau Protein Fragments

In order to prepare modified tau protein fragments, in the amino acid sequence of the tau protein which consists of 441 amino acids, four modified tau protein fragments, which are presumed to act in pathogenesis of Alzheimer's disease, were selected. As illustrated in FIG. 1, in the amino acid sequences of the four modified tau protein fragments located in the microtubule domain, the 12-amino acid sequence section was designated.

Specifically, the protein fragment having the $275^{th}$ to $286^{th}$ amino acid sequence section in the amino acid sequence of the tau protein in which the $280^{th}$ amino acid is acetylated was designated as K280-ac, and the protein fragment having the $226^{th}$ to $236^{th}$ amino acid sequence section in the amino acid sequence of the tau protein in which the $231^{st}$ amino acid is phosphorylated was designated as pT231. In addition, the protein fragment having the $381^{st}$ to $391^{st}$ amino acid sequence section in the amino acid sequence of the tau protein in which the C-terminus of the $391^{st}$ amino acid is truncated was designated as Glu391, and the protein fragment having the $303^{rd}$ to $316^{th}$ amino acid sequence section in the amino acid sequence of the tau protein in which the $306^{th}$ to $311^{th}$ amino acids are acetylated was designated as VQIVYK-ac. The K280-ac, pT231, Glu391, and VQIVYK-ac protein fragments were produced by making a request to Peptron.

II. Identification of Therapeutic Effects of Modified Tau Protein Fragments Using Animal Model Tau-P301L dementia mice were actively immunized by administration of the four modified tau protein fragments prepared in Preparation Example 1. Then, the Tau-P301L dementia mice were subjected to memory tests such as fear conditioning test and Morris water maze test, motor ability tests such as grip strength test and vertical test, and the like, so that improved effects obtained by the respective modified tau protein fragments were compared. Among the four modified tau protein fragments, the K280-ac fragment exhibited an improved effect at a level similar to that in normal mice.

Preparation Example 2. Preparation of Dementia Mouse Model and Active Immunization JNPL3 mice expressing Tau-P301L mutant gene were purchased from Taconic, and back-crossed with C57bl/6 mice for five generations in the experimental animal room of the Asan Institute for Life Sciences. Then, the mice were raised under a specific pathogen free (SPE) condition. For active immunization, the mice were administered, for six months starting from three months after birth at intervals of two weeks, two weeks, four weeks, four weeks, five weeks, four weeks, and one week in this order, the four modified tau protein fragments prepared in Preparation Example 1 together with keyhole limpet hemocyanin (KLH) as a carrier and an aluminum adjuvant. At this time, administration was carried out through intraperitoneal injection (IP injection).

The dementia mice which were actively immunized by administration of the K280-ac fragment were designated as Tau-P301L-K280-ac.

Among these, normal mice (wild type 2N4R) and Tau mutant mice (hereinafter referred to as Tau-P301L) to be used as controls were administered only KLH and an aluminum adjuvant.

Experimental Example 2. Identification of Characteristics of Dementia Mouse Model The Tau-P301L dementia mouse model used in experiments exhibited a difference in accumulation of the tau protein with aging as compared with the normal mice. Specifically, it was identified that a 4-month-old dementia mouse model exhibits an expression level of the tau protein similar to that in the normal mice, whereas a 12-month-old dementia mouse model showing severe dementia symptoms exhibits an expression level of the tau protein which is close to about 2 times that in the normal mice. Increased amount of acetylated tau proteins in the 12-month old dementia mouse model was identified by immunoblotting using ADEL-Y01h antibody prepared in Preparation Example 2 (FIGS. 2 and 3). In addition, in the dementia mouse model, even in a hippocampus region which is important for cognitive function, an increase in tau proteins in which lysine, the $280^{th}$ amino acid, is acetylated was identified, through immunohistochemical staining and immunoblotting (FIGS. 4 and 5).

Experimental Example 3. Identification of Antibody Production Against Modified Tau Protein Fragments In order to identify whether antibodies against the four modified tau protein fragments prepared in Preparation Example 1 were produced, the respective modified tau protein fragments or the full-length tau protein was finally administered, and then ELISA was performed using plasma.

As a result, it was identified that antibodies against the VQIVYKac (K311-ac) fragment are not well produced and antibodies against the K280-ac, pT231, or Glu391 fragment are well produced (FIGS. 6a to 6e).

Experimental Example 4. Fear Conditioning Experiment

A fear conditioning experiment was performed on the mice raised in Preparation Example 2. Specifically, prior to performing the fear conditioning experiment, the mice were tamed through a process, in which the respective mice were held by hand and allowed to move on the hand, for 5 minutes each day for 3 consecutive days.

On the day before the fear conditioning experiment, the mice were allowed to become accustomed to a training situation by being placed in the training situation for 10 minutes. Specifically, the mice were placed in an experimental cage. An experiment in which immediately after the mice are made to hear a beep sound, an electric stimulus is applied to the floor was repeated three times so that a fear conditioning learning for the beep sound was made by the mice. All tests were recorded on Limelight (Actimetrics) and a computer.

On the next day, the mice were placed again in the experimental cage for 10 minutes and a baseline freezing time was measured while the beep sound was heard. At this time, the freezing is a condition in which no movement is made other than an action for the animal to breathe. Then, the bottom of the cage was washed several times and wiped with ethanol again, so that any odor of the mice was removed. At the same time, a door of the cage was opened, and a ventilator was turned on to let the air out. Even in a case where only water is used, the same steps were carried out for consistency of situation.

As a result, as illustrated in FIG. 7, the normal mice exhibited a freezing time of about 150 seconds, and the Tau-P301L dementia mice exhibited a freezing time of 100 seconds or shorter. On the contrary, the Tau-P301L-K280-ac dementia mice, which were actively immunized with the K280-ac polypeptide, exhibited a freezing time of about 150 seconds as in the normal mice. On the other hand, the freezing time was not restored in the dementia mice which were actively immunized with the other three modified tau protein fragments.

Experimental Example 5. Grip Strength Test

A grip strength test was performed to identify muscle strength of the mice. For an iron bundle used in experiments, behavioral equipment possessed by the Asan Institute for Life Sciences was used. At this time, an iron bundle that weighs 40 g was used for the iron bundle. The mice produced in Preparation Example 2 were held by the tail end, and the forefeet of the mice were caused to be placed on the 40 g iron bundle so that the mice can grab the iron bundle. Then, the mice were lifted up to a height of about 30 cm in a state where the tail thereof was held. The time until the mice missed the iron bundle was measured and comparison was made for the respective mice.

As a result, as illustrated in FIG. 8, the normal mice exhibited a measured time for grab strength of 10 seconds or shorter, and the Tau-P301L dementia mice exhibited a measured time for grab strength of 5 seconds or shorter. On the contrary, in a case of the Tau-P301L-K280-ac dementia mice, a measured time for grab strength was about 12 seconds which is longer than that in the normal mice. On the other hand, in the dementia mice which were actively immunized with the other three modified tau protein fragments, no significant increase in the measured time for grab strength was not observed. From these results, it was identified that the grip strength of the Tau-P301L-K280-ac dementia mice is restored to that of the normal mice.

Experimental Example 6: Vertical Grid Test

A vertical grid test was performed on the mice raised in Preparation Example 2. For the vertical grid, behavioral equipment possessed by the experimental animal room of the Asan Institute for Life Sciences was used. Specifically, the mice were placed on the vertical grid device, and allowed to go up and down the vertical grid. The time until the mice dropped down from the grid was measured.

As a result, as illustrated in FIG. 9, the normal mice exhibited a measured time on the vertical grid of 10 seconds or shorter, and the Tau-P301L dementia mice exhibited a measured time on the vertical grid of 5 seconds or shorter. On the contrary, the Tau-P301L-K280-ac dementia mice exhibited a measured time on the vertical grid of 10 seconds which is the same as the measured time on the vertical grid in the normal mice. On the other hand, in the dementia mice which were actively immunized with the other three modified tau protein fragments, no significant increase in the measured time on the vertical grid was not observed.

Experimental Example 7. Water Maze Test

An underwater maze test was performed to evaluate a learning and memory ability of the mice. For the equipment and program used for the underwater maze test, behavioral equipment possessed by the experimental animal room of the Asan Institute for Life Sciences was used. Specifically, the underwater maze test took a total of 5 days. The mice were trained for 4 days in a state where a platform and a visual cue for the platform location are placed.

The learning was conducted by filling a swimming pool (1.4 m in diameter, 45 cm in depth) having a platform with water (29±0.5° C.) to a depth of about 26.5 cm, and then 1.5 L of whole milk powder was added to make water cloudy so that the mice can remember the platform with the cue only. Then, the mice were adapted to freely swim for 60 seconds and allowed to rest on the platform for 1 minute. The experiment was performed over a total of 12 times with 4 sets at three different starting positions. At the end of each test, 30 seconds of break time was given. At the end of one set, 30 to 45 minutes of break time was given.

After 4 days of learning, the test was performed on the $5^{th}$ day. In the experiment for evaluation, the platform was not placed, and the number of staying in the area where the platform has been placed was measured in order to identify whether the mice visit well the platform location using the cue only. The test time was set for the mice to arrive at the location where the platform had been placed within one minute. If the mice fail to arrive at the platform location within one minute, the mice were removed out of the swimming pool.

As a result, as illustrated in FIG. 10, the number of arrivals of the normal mice was measured as about 3 times, and the number of arrivals of the Tau-P301L dementia mice was measured as about 1 time. On the contrary, in a case of the Tau-P301L-K280-ac dementia mice, the number of arrivals was measured as about 3 times which is similar to that in the normal mice. The next highest increased number of arrivals was exhibited in the mice which were actively immunized with the Glu391 and VQIVYKac fragments, in this order. The mice which were actively immunized with the pT231 fragment exhibited the lowest number of times to arrive at the platform which is similar to that in the Tau-P301L dementia mice.

Experimental Example 8. Identification of Antibody Production Against Modified Tau Protein Through Experimental Examples 3 to 7, the K280-ac fragment that exhibits excellent antibody production and excellent therapeutic effects was selected among the four modified tau protein fragments. In addition, in order to identify whether the K280-ac fragment is effective as a vaccine, the N-terminal fragment and the K280-ac fragment of the tau protein having the amino acid sequence represented by SEQ ID NO: 31 were administered, and primary boosting and secondary boosting were performed. Then, these fragments were compared in terms of antibody production.

As illustrated in FIG. 11, it was identified that the K280-ac fragment of the tau protein exhibits higher antibody production than the N-terminal fragment thereof in the primary boosting and the secondary boosting.

Experimental Example 9. Identification of Behavior-Improving Effect of K280-Ac Fragment Behavioral experiments were conducted to identify changes in motor ability and cognitive function of the Tau-P301L dementia mice produced in Preparation Example 2. A nest building test which can identify a multimodal brain function of the mice was performed.

Specifically, two-thirds of the litter in a cage where the mice are raised was removed and four layers of sterile cotton (5 cm×5 cm) were placed in the cage. One mouse was allowed to enter one cage. The next morning, a degree of completion of the nest was analyzed.

As a result, it was identified that the Tau-P301L dementia mice exhibit about 50% decrease in building score as compared with the normal mice and that in a case of the Tau-P301L-K280-ac dementia mice, the building score thereof is restored to a level which is similar to that in the normal mice (FIGS. 12 and 13).

In addition, a rota-rod experiment was performed to identify a motor ability. Specifically, a rota-rod test was conducted for 5 days to identify a motor ability of the mice.

Specifically, the test was intended to measure how long the mice are able to stay on a rotating rotor. The mice were trained for 4 days and a motor ability thereof was measured on the $5^{th}$ day. The training was repeated three times a day, during which the time to stay on the rotor and the final rpm were measured while increasing the rpm of the rotor. On the $5^{th}$ day, the experiment was conducted under the same condition except that a result was measured only once without repeating (FIGS. 14 and 15). As a result, it was identified that the rpm and time for the Tau-P301L-K280-ac dementia mice were increased to levels which correspond to those for the normal mice (FIGS. 16 and 17).

In addition, a Y-maze experiment was performed to identify restoration of cognitive function. Specifically, A, B, and C zones were set in a Y-shaped box, and the mice were allowed to freely move for 5 minutes in a state where the B zone was blocked. One hour later, the state where the B zone was blocked was eliminated, and movement of the mice was observed for 5 minutes in a state where all zones were open. As a result, it was identified that a cognitive function of the Tau-P301L-K280-ac dementia mice is restored in the Y-maze, as compared with the Tau-P301L mice which exhibit a 50% decrease in measurement time as compared with the normal mice (FIG. 18).

In addition, a memory experiment was performed with novel object recognition. In a white box with no object (45 cm×45 cm×36 cm), the mice were allowed to freely move for 5 minutes so that they became accustomed to the space. Two identical objects were placed in the white box, and then the time spent staying around each object was measured while allowing the mice to make exploration for 5 minutes. 4 hours later, one of the objects installed was replaced with another model, and movement of the mice and the time spent staying around the object were measured for 5 minutes. It was identified that the Tau-P301L mice exhibit a 50% decrease in the time spent staying around the novel object as compared with the normal mice; however, in the Tau-P301L-K280-ac dementia mice, the time spent staying around the novel object is increased to a level which corresponds to that in the normal mice (FIG. 19).

From these results, it was identified that administration of the K280-ac fragment restores a motor ability and a cognitive function.

Experimental Example 10. Identification of Depression-Ameliorating Effect of K280-Ac Fragment A forced swimming test was conducted to identify a depression-ameliorating effect in the Tau-P301L dementia mice produced in Preparation Example 2. The experiment was conducted for a total of 2 days. On the first day, water was added up to about two-thirds of a clear 2 L beaker, and the mice were allowed to become accustomed to this situation for 15 minutes. On the second day, the mice were placed in water under the same condition as the first day, and movement of the mice was observed for 5 minutes. An index to swim in water (Swimming/S), an index to climb up along the beaker wall (Climbing/C), and an index to float in water without any movement (Immobility/I) were respectively analyzed.

As a result, it was identified that a depression-ameliorating effect is exhibited in the Tau-P301L-K280-ac dementia mice (FIGS. 20 to 22).

Experimental Example 11. Identification of Tauopathy-Alleviating Effect of K280-Ac Fragment In order to identify a tauopathy-alleviating effect following administration of the K280-ac fragment, brain tissues of the Tau-P301L-K280-ac dementia mice, the P301L-K280-ac dementia mice, and the normal mice produced in Preparation Example 2 were extracted, and western blotting and immunohistochemical staining were performed.

As a result of performing western blotting, it was identified that the Tau-P301L dementia mice exhibit an increase in phosphorylated tau proteins and acetylated tau proteins as compared with the normal mice. On the contrary, it was identified that the Tau-P301L-K280-ac dementia mice exhibit a decrease in phosphorylated tau proteins and acetylated tau proteins (FIG. 23). In particular, it was identified that the Tau-P301L dementia mice exhibit a 2-fold increase in tau proteins, in which lysine, the $280^{th}$ amino acid, is acetylated, as compared with the normal mice, and that the Tau-P301L-K280-ac dementia mice exhibit a decreased level of tau proteins which corresponds to that in the normal mice (FIG. 24).

In addition, even in immunohistochemical staining, it was identified that phosphorylated tau proteins and acetylated tau proteins are decreased in the brain tissue of the Tau-P301L-K280-ac dementia mice (FIGS. 25 and 26).

Experimental Example 12. Identification of Tau Aggregation-Mitigating Effect of K280-Ac Fragment In order to identify a tau aggregation-mitigating effect following administration of the K280-ac fragment, western blotting was performed with the cerebral cortices of the Tau-P301L-K280-ac dementia mice, the P301L-K280-ac dementia mice, and the normal mice produced in Preparation Example 2.

As a result, it was identified that the entire tau protein, phosphorylated tau proteins, and acetylated tau proteins were all decreased in cerebral cortex fractions (soluble or insoluble) of the Tau-P301L-K280-ac dementia mice (FIGS. 27 and 28).

Experimental Example 13. Identification of Synapse-Improving Effect of K280-Ac Fragment In order to identify a synapse-improving effect following administration of the K280-ac fragment, brain tissues of the Tau-P301L-K280-ac dementia mice, the P301L-K280-ac dementia mice, and the normal mice produced in Preparation Example 2 were extracted, and western blotting was performed.

As a result, it was identified that the P301L-K280-ac dementia mice exhibit a decreased expression level of synapse-related proteins such as PSD95, NMDA receptor, synaptophysin, and synapsin-1. On the contrary, it was identified that in a case of the Tau-P301L-K280-ac dementia mice, an expression level of synapse-related proteins such as PSD95, NMDA receptor, synaptophysin, and synapsin-1 is restored to that in the normal mice (FIG. 29).

Experimental Example 14. Identification of Inflammation-Improving Effect of K280-Ac Fragment In order to identify an inflammation-improving effect following administration of the K280-ac fragment, brain tissues of the Tau-P301L-K280-ac dementia mice, the P301L-K280-ac dementia mice, and the normal mice produced in Preparation Example 2 were extracted, and qPCR was performed for inflammation-related genes.

As a result, it was identified that the P301L-K280-ac dementia mice exhibit an increase in IFN-γ, IL-4 and IL-22 genes, and a decrease in IL-12 gene. On the contrary, it was identified that the Tau-P301L-K280-ac dementia mice exhibit a decrease in IFN-γ, IL-4 and IL-22 genes, and an increase in IL-12 gene, as compared with the P301L-K280-ac dementia mice (FIGS. 30 to 33).

Experimental Example 15. Identification of Antibody Distribution Induced by k280-Ac Vaccine in Brain Tissue In order to identify antibodies in brain tissues of the Tau-P301L-K280-ac dementia mice, the P301L-K280-ac dementia mice, and the normal mice produced in Preparation Example 2, cardiac perfusion was performed with cold physiological saline. Then, the brain tissues were extracted, and immunohistochemical staining and western blotting were performed for mouse immunoglobulin-G.

As a result, it was identified that antibodies are present in the Tau-P301L-K280-ac dementia mice (FIGS. 34 and 35).

Experimental Example 16. Identification of Metabolic Imaging Index-Improving Effect of K280-Ac Fragment In order to identify a metabolic imaging index-improving effect following administration of the K280-ac fragment, MR spectroscopy (MRS) was performed on the Tau-P301L-K280-ac dementia mice, the P301L-K280-ac dementia mice, and the normal mice produced in Preparation Example 2. The hippocampus was designated as a region of interest (ROI) (FIG. 36). It was identified that among various metabolic indices, about 50% decrease in N-acetyl-aspartyl-glutamic acid (NAAG) is exhibited in the P301L-K280-ac dementia mice as compared with the normal mice, and the NAAG is restored in the Tau-P301L-K280-ac dementia mice (FIG. 37).

In addition, diffusion tensor imaging (DTI), which is an examination that can evaluate structural integrity or orientation of the brain white matter, is a technique used to evaluate brain damage in early Alzheimer's disease. In pathological studies, mean diffusivity (MD) indicates average diffusivity and it has been reported that changes in MD are associated with demyelination and diffuse axonal injury. Changes in fractional anisotropy (FA) indicate an increase in structural orientation. It was identified that FA value and MD value are decreased in the corpus callosum of 9-month-old Tau-P301L dementia mice (FIGS. 38 and 39). From these results, it was identified that in the dementia mouse model, brain damage occurs and a level of NAAG is decreased.

Experimental Example 17. Identification of GCP-II-Decreasing Effect Following Administration of K280-Ac Fragment Glutamate carboxypeptidase-2 (GAG-II, folate hydrolase 1) is a NAAG peptidase that degrades NAAG. There is a possibility that an increase in GCP-II is a cause for decreased NAAG. Thus, brain tissues of the Tau-P301L-K280-ac dementia mice, the P301L-K280-ac dementia mice, and the normal mice produced in Preparation Example 2 were extracted and western blotting was performed.

As a result, it was identified that the P301L-K280-ac dementia mice exhibit an increased expression level of GCP-II. On the contrary, it was identified that the Tau-P301L-K280-ac dementia mice exhibit a decreased expression level of GCP-II which corresponds to that in the normal mice (FIG. 40).

---

The invention claimed is:

1. A vaccine comprising
an isolated modified tau protein fragment consisting of the following 12 consecutive amino acid residues:

(SEQ ID NO: 1)
Val-Gln-Ile-Ile-Asn-Lys-Lys-Leu-Asp-Leu-Ser-Asn wherein lysine at position 6 of SEQ ID NO: 1 is acetylated, as an active ingredient; and
an adjuvant selected from the group consisting of Freund's complete adjuvant, Freund's incomplete adjuvant, an aluminum adjuvant, pluronic polyol, a polyanion, a hydrocarbon emulsion, and dinitrophenol.

2. The vaccine of claim 1, which further comprises a carrier selected from the group consisting of lysolecithin, a peptide, oil, and keyhole limpet hemocyanin.

* * * * *